US007816536B2

(12) United States Patent
Davies et al.

(10) Patent No.: US 7,816,536 B2
(45) Date of Patent: Oct. 19, 2010

(54) 4-SUBSTITUTED AND 7-SUBSTITUTED INDOLES, BENZOFURANS, BENZOTHIOPHENES, BENZIMIDAZOLES, BENZOXAZOLES, AND BENZOTHIAZOLES AND METHODS FOR MAKING SAME

(75) Inventors: Huw M. L. Davies, East Amherst, NY (US); James Manning, Tonawanda, NY (US)

(73) Assignee: The Research Foundation of State University of New York, Amherst, NY (US)

(*) Notice: Subject to any disclaimer, the term of this patent is extended or adjusted under 35 U.S.C. 154(b) by 727 days.

(21) Appl. No.: 11/450,541

(22) Filed: Jun. 9, 2006

(65) Prior Publication Data

US 2007/0004787 A1  Jan. 4, 2007

Related U.S. Application Data

(60) Provisional application No. 60/689,208, filed on Jun. 10, 2005.

(51) Int. Cl.
C07D 277/62 (2006.01)
C07D 263/54 (2006.01)
C07D 235/04 (2006.01)
C07D 209/04 (2006.01)
C07D 333/52 (2006.01)
C07D 307/78 (2006.01)

(52) U.S. Cl. .............. 548/152; 548/217; 548/304.4; 548/469; 549/49; 549/462

(58) Field of Classification Search .............. 548/152, 548/217, 304.4, 469; 549/49, 462
See application file for complete search history.

(56) References Cited

U.S. PATENT DOCUMENTS

| 2,507,631 A | 5/1950 | Hartmann et al. |
| 2,957,880 A | 10/1960 | Rometsch et al. |
| 4,133,881 A | 1/1979 | Cale, Jr. et al. |
| 4,238,488 A | 12/1980 | Howe et al. |
| 4,866,048 A | 9/1989 | Calverley et al. |
| 5,036,053 A | 7/1991 | Himmelsbach et al. |
| 5,175,311 A | 12/1992 | Doyle |
| 5,296,595 A | 3/1994 | Doyle |
| 5,401,732 A | 3/1995 | Calverley et al. |
| 5,591,854 A | 1/1997 | Davies |
| 5,665,890 A | 9/1997 | Jacobsen et al. |
| 5,760,055 A | 6/1998 | Davies |
| 6,410,746 B1 | 6/2002 | Davies |
| 6,762,304 B2 | 7/2004 | Davies |
| 6,962,891 B2 | 11/2005 | Davies et al. |
| 7,030,051 B2 | 4/2006 | Davies |

FOREIGN PATENT DOCUMENTS

GB  2 260 903 A  5/1993

WO  00/64583  11/2000
WO  WO 2004/058174  7/2004

OTHER PUBLICATIONS

Plieninger et al. "Synthesis and incorporation of 4-[(E)-4-hydroxy-3-methyl-2-butenyl-(4-14C)]tryptophan and -tryptamine in clavine alkaloids" CAS Acession No. 1971:420097.*
Michrowska et al., Non-Substituted Hoveyda-Grubbs Ruthenium Carbenes: Enhancement of Catalyst Activity through Electronic Activation, J. Am. Chem. Soc., 126(30):9318-9325 (2004).
Remers et al., "Synthesis of Indoles from 4-Oxo-4,5,6,7-Tetetrahydroindoles. III. Introduction of Substituents by Electrophilic Substitution," J. Org. Chem., 36(9):1241-1247 (1971).
Asprou et al., "Studies on Sulphur Heterocycles. Reactions of 6,7-Dihydrobenzo[b]thiophen-4(5H)one Derivatives and their Conversion to 7-Substituted Thieno[2,3-h][1]benzopyran-8-ones," J. Heterocyclic Chem., 17:87-92 (1980).
Narayanan et al., "Novel Synthesis of Omega-(Diphenylphosphinyl)alkylcarboxylic Acids from Triphenyl-omega-Carboxyalkyl-phosphonium Salts," J. Org. Chem., 45(11):2240-2243 (1980).
Harrington et al., "Palladium-Catalyzed Reactions in the Synthesis of 3- and 4-Substituted Indoles. Approaches to Ergot Alkaloids," J. Org. Chem., 49(15):2657-2662 (1984).
Somei et al., "A Practical One Pot Synthesis of 4-Alkoxy-3-Formylindoles," Heterocycles, 22(4):797-801 (1984).
Hayakawa et al., "A New Approach to the Efficient Indole Synthesis by Allene Intramolecular Cycloaddition," Tetrahedron Lett., 27(16):1837-1840 (1986).
Padwa et al., "Intramolecular Cyclopropanation Reaction of Furanyl Diazo Ketones," J. Org. Chem., 54(2):299-308 (1989).
Iwao, "Directed Lithiation of 1-Triisopropylsilylgramine. A Short Access to 3,4-Disubstituted Indoles," Heterocycles, 36(1):29-32 (1993).
Davies, "Reaction of Metal-Stabilized Carbenoids with Pyrroles," In Advances in Nitrogen Heterocycles, Moody, ed., London: JAI Press (1995) vol. 1, pp. 1-18.
Davies et al., "Enantioselective Synthesis of Functionalized Tropanes by Rhodium(II) Carboxylate-Catalyzed Decomposition of Vinyldiazomethanes in the Presence of Pyrroles," J. Org. Chem., 62(4):1095-1105 (1997).
Thoresen et al., "Synthesis of 3,5-Diaryl-4,4-difluoro-4-bora-3a,4a-diaza-s-indacene (BODIPY) Dyes," Synlett, 1998:1276-1278 (1998).
Davies, et al. "Catalytic Asymmetric Synthesis of Diarylacetates and 4,4-Diarylbutanoates. A Formal Asymmetric Synthesis of (+)-Sertraline," Org. Lett., 1(2):233-236 (1999).

(Continued)

*Primary Examiner*—Joseph R Kosack
(74) *Attorney, Agent, or Firm*—Peter Rogalskyj, Esq

(57) ABSTRACT

Disclosed are 4-substituted and 7-substituted indoles, benzofurans, benzothiophenes, benzimidazoles, benzoxazoles, and benzothiazoles. Also disclosed are methods for making 4-substituted and 7-substituted indoles, benzofurans, benzothiophenes, benzimidazoles, benzoxazoles, and benzothiazoles, including those having the formulae. The methods include contacting a 4-substituted-6,7-dihydro indole, benzofuran, benzothiophene, benzimidazole, benzoxazole, or benzothiazole compound or a 7-substituted-4,5-dihydro indole, benzofuran, benzothiophene, benzimidazole, benzoxazole, or benzothiazole compound with a vinyldiazo compound in the presence of a dirhodium catalyst.

36 Claims, No Drawings

OTHER PUBLICATIONS

Basel et al., "Imidazole and Trifluoroethanol as Efficient and Mild Reagents for Destruction of Excess Di-tert-butyl Dicarbonate [(BOC)2O]," Synthesis, 4:550-552 (2001).

Austin et al., "Enantioselective Organocatalytic Indole Alkylations. Design of a New and Highly Effective Chiral Amine for Iminium Catalysis," J. Am. Chem. Soc., 124(7):1172-1173 (2002).

Chauder et al., "Rapid Route to 3,4-Substituted Indoles via a Directed Ortho Metalation-Retro-Mannich Sequence," Org. Lett., 4(5):815-817 (2002).

Evans et al., "Enantioselective Indole Friedel-Crafts Alkylations Catalyzed by Bis(oxazolinyl)pyridine-Scandium(III) Triflate Complexes," J. Am. Chem. Soc., 125(36):10780-10781 (2003).

Kalinin et al., "seco-C/D Ring Analogues of Ergot Alkaloids. Synthesis via Intramolecular Heck and Ring-Closing Metathesis Reactions," Org. Lett., 5(19):3519-3521 (2003).

Maekawa et al., "Enantioselective Electrochemical Oxidation of Enol Acetates Using a Chiral Supporting Electrolyte," Chirality, 15(1):95-100 (2003).

Davies et al., "Asymmetric Catalysis Special Feature Part I: Catalytic Asymmetric Reactions for Organic Synthesis: The Combined C-H Activation/Cope Rearrangement," Proc. Natl. Acad. Set. U.S.A., 101(15):5472-5475 (2004).

Davies et al., "Catalytic Asymmetric Reactions for Organic Synthesis: The Combined C-H Activation/Siloxy-Cope Rearrangement," J. Org. Chem., 69(26):9241-9247 (2004).

Davies et al., "Highly Diastereoselective and Enantioselective C-H Functionalization of 1,2-Dihydronaphthalenes: A Combined C-H Activation/Cope Rearrangement Followed by a Retro-Cope Rearrangement," J. Am. Chem. Soc., 126(35):10862-10863 (2004).

Davies et al., "Direct Synthesis of (+)-Erogorgiaene Through a Kinetic Enantiodifferentiating Step," Angew. Chem. Int. Ed., 44(11):1733-1735 (2005).

Davies et al., "Enantioselective Double C-H Activation of Dihydronaphthalenes," Org. Lett., 7(12):2293-2296 (2005).

Dunetz et al., "Synthesis of Highly Substituted Indolines and Indoles via Intramolecular [4+2] Cycloaddition of Ynamides and Conjugated Enynes," J. Am. Chem. Soc., 127(16):5776-5777 (2005).

Evans et al., "Enantioselective Friedel-Crafts Alkylations of , alpha,beta-Unsaturated 2-Acyl Imidazoles Catalyzed by Bis(oxazolinyl)pyridine-Scandium(III) Triflate Complexes," J. Am. Chem. Soc., 127(25):8942-8943 (2005).

Huang et al., "Enantioselective Organo-Cascade Catalysis," J. Am. Chem. Soc., 127(43):15051-15053 (2005).

Palomo et al., "Highly Enantioselective Friedel-Crafts Alkylations of Pyrroles and Indoles with alpha'-Hydroxy Enones under Cu(II)-Simple Bis(oxazoline) Catalysis," J. Am. Chem. Soc., 127(12):4154-4155 (2005).

Davies et al., "Combined C-H Activation/Cope Rearrangement as a Strategic Reaction in Organic Synthesis: Total Synthesis of (−)-Colombiasin A and (−)-Elisapterosin B," J. Am. Chem. Soc., 128(7):2485-2490 (2006).

Davies et al., "C-H Activation as a Strategic Reaction: Enantioselective Synthesis of 4-Substituted Indoles," J. Am. Chem. Soc., 128:1060-1061 (2006).

Plieninger et al., "Synthese von 4-[E-4-Hydroxy-3-methyl-delta2-butenyl]-tryptophan-[4−14C] sowie-tryptamin-[4−14C] und Einbau in Clavin-Alkaloide," *Justus Liebigs Annalen der Chemie*, 743:95-111 (1971).

\* cited by examiner

4-SUBSTITUTED AND 7-SUBSTITUTED INDOLES, BENZOFURANS, BENZOTHIOPHENES, BENZIMIDAZOLES, BENZOXAZOLES, AND BENZOTHIAZOLES AND METHODS FOR MAKING SAME

The present application claims the benefit of U.S. Provisional Patent Application Ser. No. 60/689,208 filed Jun. 10, 2005, which provisional patent application is hereby incorporated by reference.

The present invention was made with the support of the National Science Foundation Contract Nos. CHE0092490 and CHE0350536. The Federal Government may have certain rights in this invention.

FIELD OF THE INVENTION

The present invention relates to methods and intermediates that can be used to make heterocyclic compounds and, more particularly, to methods and intermediates that can be used to make 4-substituted and 7-substituted indoles, benzofurans, benzothiophenes, benzimidazoles, benzoxazoles, and benzothiazoles.

BACKGROUND OF THE INVENTION

Heterocyclic compounds, such as indoles, benzofurans, benzothiophenes, benzimidazoles, benzoxazoles, and benzothiazoles, are important materials in the pharmaceutical and other industries. For example, the indole nucleus has long been of great interest to synthetic chemists owing to its ubiquity in a large number of biologically active alkaloids, pharmaceutical agents and natural products (Sundberg, *Indoles*, London: Academic Press (1996), which is hereby incorporated by reference.)

Traditional strategies for the synthesis of functionalized variants of this "privileged" moiety have relied largely upon cyclization of an appropriately substituted precursor (Hayakawa et al., "A New Approach to the Efficient Indole Synthesis by Allene Intramolecular Cycloaddition," *Tetrahedron Lett.*, 27(16):1837-1840 (1986); and Dunetz et al., "Synthesis of Highly Substituted Indolines and Indoles via Intramolecular [4+2] Cycloaddition of Ynamides and Conjugated Enynes," *J. Am. Chem. Soc.*, 127(16):5776-5777 (2005), which are hereby incorporated by reference); metallation followed by electrophilic trapping of the anion (Iwao, *Heterocycles*, 36:29-32 (1993) ("Iwao"), and Chauder et al., "Rapid Route to 3,4-Substituted Indoles via a Directed Ortho Metalation-Retro-Mannich Sequence," *Org. Lett.*, 4(5):815-817 (2002), which are hereby incorporated by reference); and cross-coupling reactions. Recently, attention has been focused on the asymmetric functionalization of the indole core (Austin et al., "Enantioselective Organocatalytic Indole Alkylations. Design of a New and Highly Effective Chiral Amine for Iminium Catalysis," *J. Am. Chem. Soc.*, 124(7): 1172-1173 (2002), and Palomo et al., "Highly Enantioselective Friedel-Crafts Alkylations of Pyrroles and Indoles with α'-Hydroxy Enones under Cu(II)-Simple Bis(oxazoline) Catalysis," *J. Am. Chem. Soc.*, 127(12):4154-4155 (2005), which are hereby incorporated by reference). These examples take advantage of the relatively nucleophilic 3-position of the indole nucleus to add electrophiles via a Friedel-Crafts type reaction and are shown schematically below:

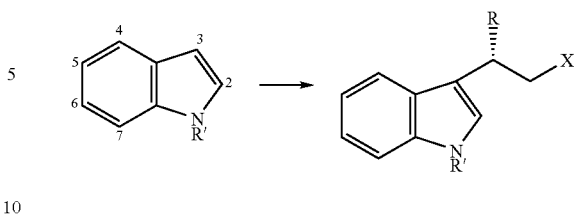

Other positions on the indole nucleus, as well as those on other heterocyclic nuclei, (e.g., the 4- and 7-positions) are more difficult to functionalize. For example, the 4-position in indoles is notoriously difficult to functionalize using electrophilic substitution chemistry. There are comparatively few methods for selective functionalization of this less reactive position. Such methods include a thallation/iodination reaction (Somei et al., *Heterocycles*, 22:797-801 (1984), which is hereby incorporated by reference); directed lithiation of 3-substituted gramines (Iwao, which is hereby incorporated by reference); and other metallation/substitution reactions.

A need continues to exist for synthetic methods for the preparation of substituted indoles, benzofurans, benzothiophenes, benzimidazoles, benzoxazoles, and benzothiazoles, and for intermediates useful in such methods. The present invention is directed to addressing this need.

SUMMARY OF THE INVENTION

The present invention relates to a method for making a 4-substituted indole, benzofuran, benzothiophene, benzimidazole, benzoxazole, or benzothiazole. The method includes providing a 4-substituted-6,7-dihydro indole, benzofuran, benzothiophene, benzimidazole, benzoxazole, or benzothiazole compound having the formula:

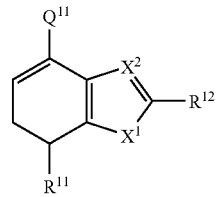

wherein $Q^{11}$ is a leaving group; wherein $X^1$ is N-$Q^{12}$, O, or S; wherein $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group; and wherein $R^{12}$ and $R^3$ are independently selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group, or wherein $R^{12}$ and $R^3$, taken together with the carbon atoms to which they are bonded, form a 5-12 membered ring. The method further includes providing a diazovinyl compound having the formula:

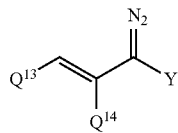

wherein $Q^{13}$ is an alkyl group or an aryl group, and wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentene or cyclohexene ring); and wherein Y is an electron withdrawing group. The method also includes contacting the 4-substituted-6,7-dihydro indole, benzofuran, benzothiophene, benzimidazole, benzoxazole, or benzothiazole compound with the vinyldiazo compound in the presence of a dirhodium catalyst under conditions effective to produce a compound having the formula:

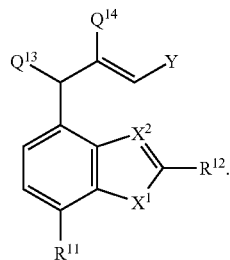

The present invention also relates to a compound having the formula:

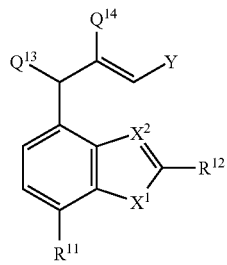

wherein $X^1$ is N-$Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentyl or cyclohexyl ring); and wherein Y is an electron withdrawing group.

The present invention also relates to a compound having the formula:

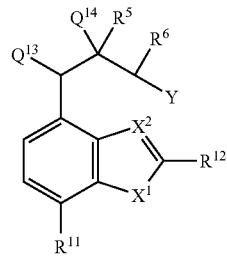

that is enriched in an enantiomer having one of the following formulae:

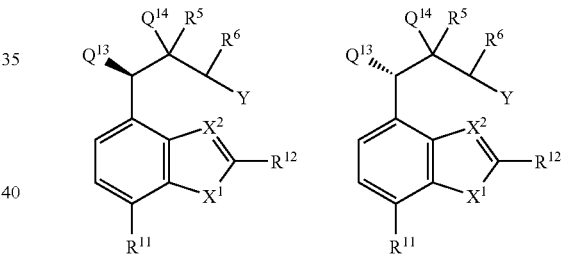

wherein $X^1$ is N-$Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentyl or cyclohexyl ring); wherein Y is an electron withdrawing group, a aldehyde group, or a —CH$_2$OH or other alkyl group; and wherein each of $R^5$ and $R^6$ is a hydrogen atom, or wherein $R^5$ and $R^6$, taken together, represent a second bond between the carbon atoms to which they are bonded.

The present invention also relates to a method for making a 7-substituted indole, benzofuran, benzothiophene, benzimidazole, benzoxazole, or benzothiazole. The method includes providing a 7-substituted-4,5-dihydro indole, benzofuran, benzothiophene, benzimidazole, benzoxazole, or benzothiazole compound having the formula:

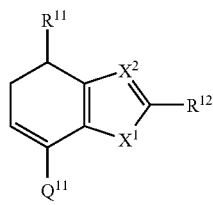

wherein $Q^{11}$ is a leaving group; wherein $X^1$ is N-$Q^{12}$, O, or S; wherein $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group; and wherein $R^{12}$ and $R^3$ are independently selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group, or wherein $R^{12}$ and $R^3$, taken together with the carbon atoms to which they are bonded, form a 5-12 membered ring. The method further includes providing a diazovinyl compound having the formula:

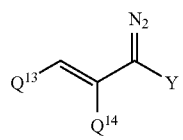

wherein $Q^{13}$ is an alkyl group or an aryl group, and wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentene or cyclohexene ring); and wherein Y is an electron withdrawing group. The method further includes contacting the 7-substituted-4,5-dihydro indole, benzofuran, benzothiophene, benzimidazole, benzoxazole, or benzothiazole compound with the vinyldiazo compound in the presence of a dirhodium catalyst under conditions effective to produce a compound having the formula:

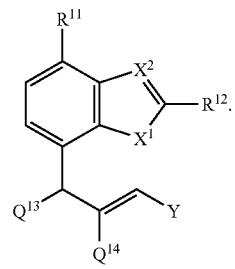

The present invention also relates to a compound having the formula:

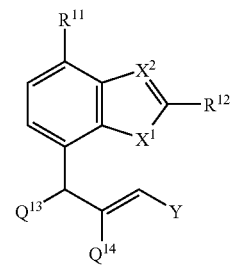

wherein $X^1$ is N-$Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentyl or cyclohexyl ring); and wherein Y is an electron withdrawing group.

The present invention also relates to a compound having the formula:

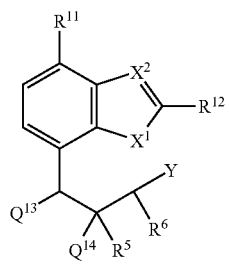

that is enriched in an enantiomer having one of the following formulae:

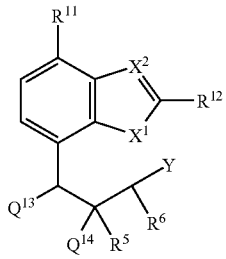 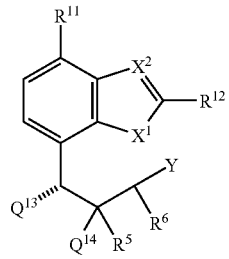

wherein $X^1$ is $N-Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is $C-R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentyl or cyclohexyl ring); wherein Y is an electron withdrawing group, a aldehyde group, or a —$CH_2OH$ or other alkyl group; and wherein each of $R^5$ and $R^6$ is a hydrogen atom, or wherein $R^5$ and $R^6$, taken together, represent a second bond between the carbon atoms to which they are bonded.

DETAILED DESCRIPTION OF THE INVENTION

We have discovered a very effective method to generate 4-substituted indoles. We have also discovered that this method can be carried out in a highly enantioselective manner (strong preference for the formation of the possible mirror images). This could be a very useful building block from making pharmaceutical agents. The methods can also be used to enantioselectively prepare 4-substituted benzofurans, benzothiophenes, benzimidazoles, benzoxazoles, and benzothiazoles. Additionally, the methods can also be used to prepare 7-substituted indoles, benzofurans, benzothiophenes, benzimidazoles, benzoxazoles, and benzothiazoles, and the methods can provide a convenient route to the enantioselective synthesis of 7-substituted indoles, benzofurans, benzothiophenes, benzimidazoles, benzoxazoles, and benzothiazoles.

As used herein, "4-substituted indole" is meant to refer to any compound having an indole ring system and a substituent at the indole ring system's 4 position. The other positions on the indole ring system can be substituted or unsubstituted.

As used herein, "4-substituted benzofuran" is meant to refer to any compound having a benzofuran ring system and a substituent at the benzofuran ring system's 4 position. The other positions on the benzofuran ring system can be substituted or unsubstituted.

As used herein, "4-substituted benzothiophene" is meant to refer to any compound having a benzothiophene ring system and a substituent at the benzothiophene ring system's 4 position. The other positions on the benzothiophene ring system can be substituted or unsubstituted.

As used herein, "4-substituted benzimidazole" is meant to refer to any compound having a benzimidazole ring system and a substituent at the benzimidazole ring system's 4 position. The other positions on the benzimidazole ring system can be substituted or unsubstituted.

As used herein, "4-substituted benzoxazole" is meant to refer to any compound having a benzoxazole ring system and a substituent at the benzoxazole ring system's 4 position. The other positions on the benzoxazole ring system can be substituted or unsubstituted.

As used herein, "4-substituted benzothiazole" is meant to refer to any compound having a benzothiazole ring system and a substituent at the benzothiazole ring system's 4 position. The other positions on the benzothiazole ring system can be substituted or unsubstituted.

The present invention, in one aspect thereof, relates to a method for making a 4-substituted indole, benzofuran, benzothiophene, benzimidazole, benzoxazole, or benzothiazole. The method includes providing a 4-substituted-6,7-dihydro indole, benzofuran, benzothiophene, benzimidazole, benzoxazole, or benzothiazole compound having the formula:

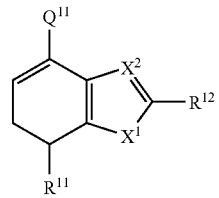

wherein $Q^{11}$ is a leaving group; wherein $X^1$ is $N-Q^{12}$, O, or S; wherein $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is $C-R^3$ or N; wherein $R^{11}$ is selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group; and wherein $R^{12}$ and $R^3$ are independently selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group, or wherein $R^{12}$ and $R^3$, taken together with the carbon atoms to which they are bonded, form a 5-12 membered ring.

The method further includes providing a diazovinyl compound having the formula:

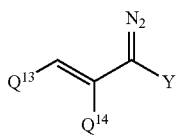

wherein $Q^{13}$ is an alkyl group or an aryl group, and wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentene or cyclohexene ring); and wherein Y is an electron withdrawing group.

The method also includes contacting the 4-substituted-6,7-dihydro indole, benzofuran, benzothiophene, benzimidazole, benzoxazole, or benzothiazole compound with the vinyldiazo compound in the presence of a dirhodium catalyst under conditions effective to produce a compound having the formula:

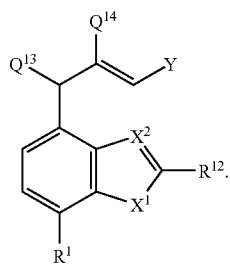

Illustratively, the 4-substituted-6,7-dihydro indole, benzofuran, benzothiophene, benzimidazole, benzoxazole, or benzothiazole compound can be contacted with the vinyldiazo compound in any suitable solvent, examples of which include alkane solvents (e.g., hexanes, 2,2-dimethylbutane, etc.), aromatic solvents (e.g., benzene, toluene, trifluorotoluene, etc.), and combinations thereof (e.g., a hexanes/toluene mixture). The 4-substituted-6,7-dihydro indole, benzofuran, benzothiophene, benzimidazole, benzoxazole, or benzothiazole compound and the vinyldiazo compound can be reacted in any suitable mole ratio, such as 4-substituted-6,7-dihydro indole, benzofuran, benzothiophene, benzimidazole, benzoxazole, or benzothiazole compound:vinyldiazo compound mole ratios of from about 5:1 to about 1:5, such as from about 4:1 to about 1:4, from about 3:1 to about 1:3 from about 2:1 to about 1:2, from about 1.8:1 to about 1:1.8, from about 1.5:1 to about 1:1.5, from about 1.4:1 to about 1:1.4, from about 1.3:1 to about 1:1.3, from about 1.2:1 to about 1:1.2, from about 1.1:1 to about 1:1.1, from about 1.05:1 to about 1:1.05, and/or about 1:1. The reaction can be carried out at any suitable temperature, such from about 0° C. to about the boiling point of the solvent being employed, from about 0° C. to about room temperature, from about room temperature to about the boiling point of the solvent, from about 0° C. to about 100° C., from about 0° C. to about 80° C., from about 0° C. to about 70° C., from about 0° C. to about 60° C., from about 0° C. to about 50° C., etc. The amount of dirhodium catalyst present can be from about 0.05 mol % to about 10 mol %, such as from about 0.1 mol % to about 5 mol %, from about 0.2 mol % to about 2 mol %, from about 0.25 mol % to about 1 mol %, from about 0.3 mol % to about 0.8 mol %, from about 0.4 mol % to about 0.6 mol %, and/or about 0.5 mol %, based, for example, on the number of moles of the limiting reactant present in the reaction.

As indicated above, $Q^{11}$ is a leaving group. The ability of a group to act as a leaving group (e.g., in a nucleophilic substitution or elimination reaction) depends on its standalone stability as an anion, and on the strength of its bond to carbon, and both of these factors correlate well with its Brønsted basicity. This is often given as the pKa of the conjugate acid. The lower the pKa, the better the leaving group as a general rule. For example, groups with a (conjugate acid) pKa of 6 or less can be good leaving groups for use in the practice of the present invention. Illustratively, suitable leaving groups include those having a (conjugate acid) pKa of less than 6, less than 5.5, less than 5, less than 4.5, less than 4, less than 3.5, less than 3, less than 2.5, less than 2, less than 1.5, less than 1, less than 0.5, and/or less than 0. For example, $Q^{11}$ can be a halogen atom, an alkyl sulfonate group (e.g., a triflate group, a mesylate group, etc.), an aryl sulfonate group (e.g., a tosylate group), and an acyloxy group (e.g., a acetoxy group).

As discussed above, $Q^{13}$ can be an alkyl group or an aryl group. As illustrative examples of suitable alkyl groups, there can be mentioned unsubstituted C1-C12 alkyl groups, unsubstituted C1-C8 alkyl groups, unsubstituted C1-C6 alkyl groups, unsubstituted C1-C4 alkyl groups, substituted C1-C12 alkyl groups, substituted C1-C8 alkyl groups, substituted C1-C6 alkyl groups, substituted C1-C4 alkyl groups, methyl, ethyl, n-propyl, i-propyl, n-butyl i-butyl, t-butyl, cyclohexyl, cyclopentyl, cyclohexenyl, cyclopentenyl, and the like. As illustrative examples of suitable aryl groups, there can be mentioned 5-20 membered homocyclic rings, 5-20 membered heterocyclic rings, 5-10 membered homocyclic rings, 5-10 membered heterocyclic rings, phenyl, naphthyl, pyridyl, and the like, which can be unsubstituted or substituted with, for example, one or more alkyls, alkoxys, halogens, or combinations thereof. As further illustration, $Q^{13}$ can be a moiety having the formula $-Q^5-Q^6$, where $Q^5$ is a C1-C12 saturated or unsaturated alkylene moiety, optionally containing one or more heteroatoms and where $Q^6$ is a substituted or unsubstituted, 5-20 membered, heterocyclic or homocyclic ring; such as in the case where $-Q^5-$ is an unsaturated alkylene moiety having the formula —CH=CH—, as in the case where $Q^6$ is a substituted or unsubstituted phenyl ring, and such as in the case where $-Q^5-$ is an unsaturated alkylene moiety having the formula —CH=CH— and $Q^6$ is a substituted or unsubstituted phenyl ring.

Also as discussed above, $Q^{14}$ can be a hydrogen atom, an alkyl group, or an aryl group. As illustrative examples of suitable alkyl groups, there can be mentioned unsubstituted C1-C12 alkyl groups, unsubstituted C1-C8 alkyl groups, unsubstituted C1-C6 alkyl groups, unsubstituted C1-C4 alkyl groups, substituted C1-C12 alkyl groups, substituted C1-C8 alkyl groups, substituted C1-C6 alkyl groups, substituted C1-C4 alkyl groups, methyl, ethyl, n-propyl, i-propyl, n-butyl i-butyl, t-butyl, cyclohexyl, cyclopentyl, cyclohexenyl, cyclopentenyl, and the like. As illustrative examples of suitable aryl groups, there can be mentioned 5-20 membered homocyclic rings, 5-20 membered heterocyclic rings, 5-10 membered homocyclic rings, 5-10 membered heterocyclic rings, phenyl, naphthyl, pyridyl, and the like, which can be unsubstituted or substituted with, for example, one or more alkyls, alkoxys, halogens, or combinations thereof.

Also as discussed above, $Q^{13}$ and $Q^{14}$, taken together with the carbon atoms to which they are bonded, can represent a 5-12 membered ring. The 5-12 membered ring can be homocyclic or heterocyclic, substituted or unsubstituted, monocyclic or polycyclic. Illustratively, the 5-12 membered ring can be a substituted or unsubstituted 5- or 6-membered ring (e.g., a cyclopentyl ring or a cyclohexyl ring).

In certain embodiments, the method of the present invention can be used to prepare 4-substituted indoles, for example, by using a 4-substituted-6,7-dihydro indole having the formula:

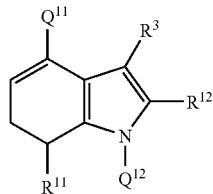

and contacting the 4-substituted-6,7-dihydro indole with the vinyldiazo compound in the presence of a dirhodium catalyst under conditions effective to produce a compound having the formula:

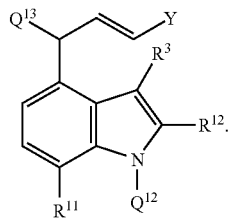

In other embodiments, the method of the present invention can be used to prepare a 4-substituted benzofuran, for example, by using a 4-substituted-6,7-dihydro benzofuran having the formula:

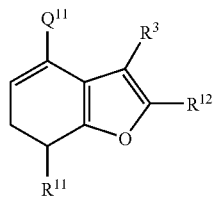

and contacting the 4-substituted-6,7-dihydro benzofuran with the vinyldiazo compound in the presence of a dirhodium catalyst under conditions effective to produce a compound having the formula:

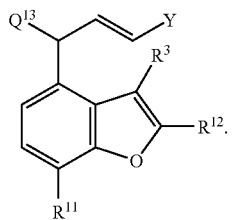

In still other embodiments, the method of the present invention can be used to prepare a 4-substituted benzothiophene, for example, by using a 4-substituted-6,7-dihydro benzothiophene having the formula:

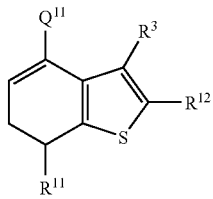

and contacting the 4-substituted-6,7-dihydro benzothiophene with the vinyldiazo compound in the presence of a dirhodium catalyst under conditions effective to produce a compound having the formula:

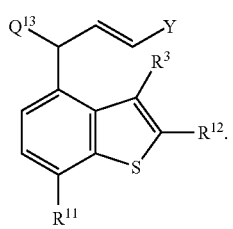

In yet other embodiments, the method of the present invention can be used to prepare a 4-substituted benzimidazole, for example, by using a 4-substituted-6,7-dihydro benzimidazole having the formula:

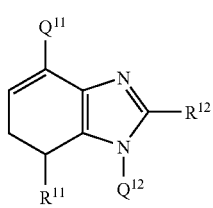

and contacting the 4-substituted-6,7-dihydro benzimidazole with the vinyldiazo compound in the presence of a dirhodium catalyst under conditions effective to produce a compound having the formula:

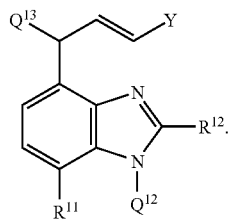

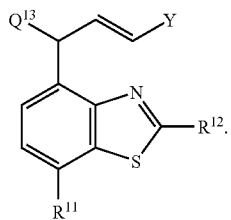

In still other embodiments, the method of the present invention can be used to prepare a 4-substituted benzoxazole, for example, by using a 4-substituted-6,7-dihydro benzoxazole having the formula:

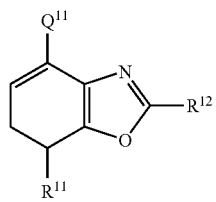

and contacting the 4-substituted-6,7-dihydro benzoxazole with the vinyldiazo compound in the presence of a dirhodium catalyst under conditions effective to produce a compound having the formula:

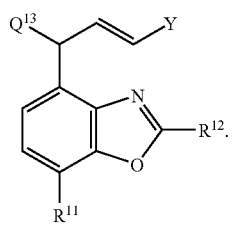

In yet other embodiments, the method of the present invention can be used to prepare a 4-substituted benzothiazole, for example, by using a 4-substituted-6,7-dihydro benzothiazole having the formula:

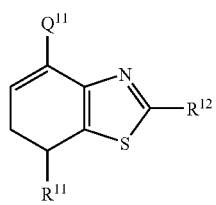

and contacting the 4-substituted-6,7-dihydro benzothiazole with the vinyldiazo compound in the presence of a dirhodium catalyst under conditions effective to produce a compound having the formula:

Using the methods of the present invention, compounds having the formula:

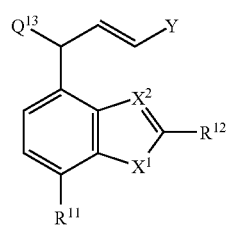

can be enriched in one or the other enantiomer, i.e., in an enantiomer having the formula:

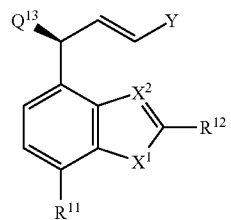

or in an enantiomer having the formula:

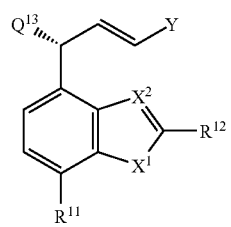

Such enantiomeric enrichment (e.g., >50% ee, >55% ee, >60% ee, >70% ee, >80% ee, >85% ee, >90% ee, >95% ee, >98% ee, and/or >99% ee) can be achieved by contacting the 4-substituted-6,7-dihydro indole, benzofuran, benzothiophene, benzimidazole, benzoxazole, or benzothiazole compound with the vinyldiazo compound in the presence of a dirhodium catalyst having $D_2$ symmetry under conditions effective to selectively produce compounds having the formula:

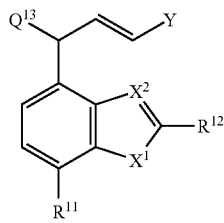

that are enriched in one or the other enantiomer.

It will be appreciated that the methods of the present invention for making 4-substituted indoles, benzofurans, benzothiophenes, benzimidazoles, benzoxazoles, or benzothiazoles can, optionally, include additional steps, for example, to convert compounds having the formula:

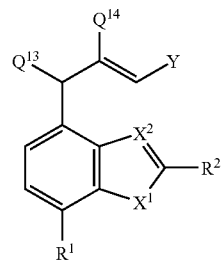

to other 4-substituted indoles, benzofurans, benzothiophenes, benzimidazoles, benzoxazoles, or benzothiazoles.

Illustratively, in the case where $X^1$ is an N-$Q^{12}$ group, where $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group, the method of the present invention can further include a step in which the N-$Q^{12}$ group is converted to an N—H group. This step can be carried out by any suitable method, such as by treating the compound in which $X^1$ is N-$Q^{12}$ with a strong acid.

As further illustration, the methods of the present invention for making 4-substituted indoles, benzofurans, benzothiophenes, benzimidazoles, benzoxazoles, or benzothiazoles can, optionally, include additional steps, for example, to convert compounds having the formula:

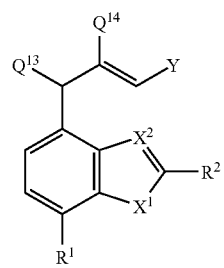

to 4-substituted indoles, benzofurans, benzothiophenes, benzimidazoles, benzoxazoles, or benzothiazoles having the formula:

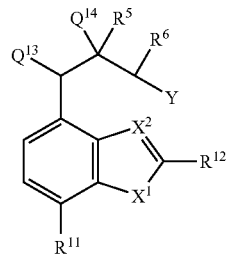

in which Y is an electron withdrawing group, a aldehyde group, or a —$CH_2OH$ or other alkyl group; and in which each of $R^5$ and $R^6$ is a hydrogen atom, or in which $R^5$ and $R^6$, taken together, represent a second bond between the carbon atoms to which they are bonded. For example, in the case where Y is a carboxylic (e.g., acid, ester, etc.) electron withdrawing group, the conversion of the Y electron withdrawing group to an aldehyde group, or to a —$CH_2OH$ group, or to another alkyl group, can be readily achieved, for example, by the use of a suitable reducing agent and a combination of suitable reducing agents. Additionally or alternatively, compounds in which $R^5$ and $R^6$, taken together, represent a second bond between the carbon atoms to which they are bonded can be converted to compounds in which each of $R^5$ and $R^6$ is a hydrogen atom, for example by catalytic hydrogenation.

It will be appreciated that the methods of the present invention can be used to prepare compounds having the formula:

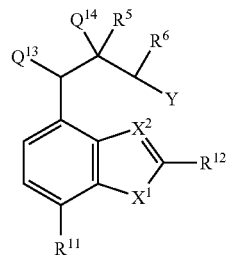

that are enriched (e.g., >50% ee, >55% ee, >60% ee, >70% ee, >80% ee, >85% ee, >90% ee, >95% ee, >98% ee, and/or >99% ee) in one or the other enantiomer, i.e., in an enantiomer having the formula:

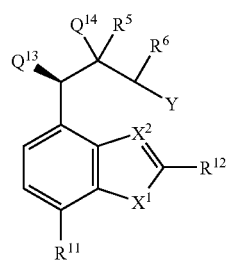

or in an enantiomer having the formula:

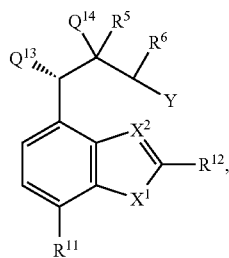

and the present invention, in another aspect thereof, relates to such compounds. In certain embodiments, in such enantiomerically enriched compounds, $R^{11}$ is a carboxylic acid group, a hydroxy group, or a thiol group. In other embodiments, $R^{11}$ is not a carboxylic acid group. In still other embodiments, $R^{11}$ is not a hydroxy group. In yet other embodiments, $R^{11}$ is not a thiol group. In still other embodiments, $R^{11}$ is not a carboxylic acid group, a hydroxy group, or a thiol group. In certain embodiments, in such enantiomerically enriched compounds, $R^{12}$ is a carboxylic acid group, a hydroxy group, or a thiol group. In other embodiments, $R^{12}$ is not a carboxylic acid group. In still other embodiments, $R^{12}$ is not a hydroxy group. In yet other embodiments, $R^{12}$ is not a thiol group. In still other embodiments, $R^{12}$ is not a carboxylic acid group, a hydroxy group, or a thiol group. In certain embodiments, in such enantiomerically enriched compounds, $R^3$ is a carboxylic acid group, a hydroxy group, or a thiol group. In other embodiments, $R^3$ is not a carboxylic acid group. In still other embodiments, $R^3$ is not a hydroxy group. In yet other embodiments, $R^3$ is not a thiol group. In still other embodiments, $R^3$ is not a carboxylic acid group, a hydroxy group, or a thiol group. In certain embodiments, in such enantiomerically enriched compounds, $R^{11}$ is not a carboxylic acid group, a hydroxy group, or a thiol group; $R^{12}$ is not a carboxylic acid group, a hydroxy group, or a thiol group; and $R^3$ is not a carboxylic acid group, a hydroxy group, or a thiol group.

As discussed above, the present invention also relates to a method for making 7-substituted indoles, benzofurans, benzothiophenes, benzimidazoles, benzoxazoles, and benzothiazoles, and the methods can provide a convenient route to the enantioselective synthesis of 7-substituted indoles, benzofurans, benzothiophenes, benzimidazoles, benzoxazoles, and benzothiazoles.

As used herein, "7-substituted indole" is meant to refer to any compound having an indole ring system and a substituent at the indole ring system's 7 position. The other positions on the indole ring system can be substituted or unsubstituted.

As used herein, "7-substituted benzofuran" is meant to refer to any compound having a benzofuran ring system and a substituent at the benzofuran ring system's 7 position. The other positions on the benzofuran ring system can be substituted or unsubstituted.

As used herein, "7-substituted benzothiophene" is meant to refer to any compound having a benzothiophene ring system and a substituent at the benzothiophene ring system's 7 position. The other positions on the benzothiophene ring system can be substituted or unsubstituted.

As used herein, "7-substituted benzimidazole" is meant to refer to any compound having a benzimidazole ring system and a substituent at the benzimidazole ring system's 7 position. The other positions on the benzimidazole ring system can be substituted or unsubstituted.

As used herein, "7-substituted benzoxazole" is meant to refer to any compound having a benzoxazole ring system and a substituent at the benzoxazole ring system's 7 position. The other positions on the benzoxazole ring system can be substituted or unsubstituted.

As used herein, "7-substituted benzothiazole" is meant to refer to any compound having a benzothiazole ring system and a substituent at the benzothiazole ring system's 7 position. The other positions on the benzothiazole ring system can be substituted or unsubstituted.

The present invention, in one aspect thereof, relates to a method for making a 7-substituted indole, benzofuran, benzothiophene, benzimidazole, benzoxazole, or benzothiazole. The method includes providing a 7-substituted-4,5-dihydro indole, benzofuran, benzothiophene, benzimidazole, benzoxazole, or benzothiazole compound having the formula:

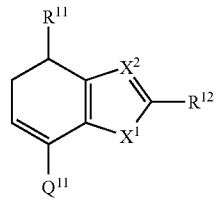

wherein $Q^{11}$ is a leaving group; wherein $X^1$ is N-$Q^{12}$, O, or S; wherein $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group; and wherein $R^{12}$ and $R^3$ are independently selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group, or wherein $R^{12}$ and $R^3$, taken together with the carbon atoms to which they are bonded, form a 5-12 membered ring.

The method further includes providing a diazovinyl compound having the formula:

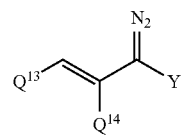

wherein $Q^{13}$ is an alkyl group or an aryl group, and wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentene or cyclohexene ring); and wherein Y is an electron withdrawing group.

The method also includes contacting the 7-substituted-4, 5-dihydro indole, benzofuran, benzothiophene, benzimidazole, benzoxazole, or benzothiazole compound with the vinyldiazo compound in the presence of a dirhodium catalyst under conditions effective to produce a compound having the formula:

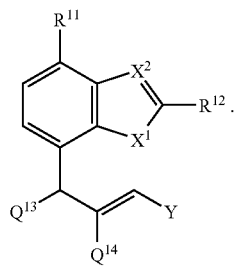

Illustratively, the 7-substituted-4,5-dihydro indole, benzofuran, benzothiophene, benzimidazole, benzoxazole, or benzothiazole compound can be contacted with the vinyldiazo compound in any suitable solvent, examples of which include alkane solvents (e.g., hexanes, 2,2-dimethylbutane, etc.), aromatic solvents (e.g., benzene, toluene, trifluorotoluene, etc.), and combinations thereof (e.g., a hexanes/toluene mixture). The 7-substituted-4,5-dihydro indole, benzofuran, benzothiophene, benzimidazole, benzoxazole, or benzothiazole compound and the vinyldiazo compound can be reacted in any suitable mole ratio, such as 7-substituted-4,5-dihydro indole, benzofuran, benzothiophene, benzimidazole, benzoxazole, or benzothiazole compound:vinyldiazo compound mole ratios of from about 5:1 to about 1:5, such as from about 4:1 to about 1:4, from about 3:1 to about 1:3 from about 2:1 to about 1:2, from about 1.8:1 to about 1:1.8, from about 1.5:1 to about 1:1.5, from about 1.4:1 to about 1:1.4, from about 1.3:1 to about 1:1.3, from about 1.2:1 to about 1:1.2, from about 1.1:1 to about 1:1.1, from about 1.05:1 to about 1:1.05, and/or about 1:1. The reaction can be carried out at any suitable temperature, such from about 0° C. to about the boiling point of the solvent being employed, from about 0° C. to about room temperature, from about room temperature to about the boiling point of the solvent, from about 0° C. to about 100° C., from about 0° C. to about 80° C., from about 0° C. to about 70° C., from about 0° C. to about 60° C., from about 0° C. to about 50° C., etc. The amount of dirhodium catalyst present can be from about 0.05 mol % to about 10 mol %, such as from about 0.1 mol % to about 5 mol %, from about 0.2 mol % to about 2 mol %, from about 0.25 mol % to about 1 mol %, from about 0.3 mol % to about 0.8 mol %, from about 0.4 mol % to about 0.6 mol %, and/or about 0.5 mol %, based, for example, on the number of moles of the limiting reactant present in the reaction.

As indicated above, $Q^{11}$ is a leaving group, and considerations for selecting suitable leaving groups in the context of making 7-substituted indoles, benzofurans, benzothiophenes, benzimidazoles, benzoxazoles, and benzothiazoles are the same as those set forth above in the context of making 4-substituted indoles, benzofurans, benzothiophenes, benzimidazoles, benzoxazoles, and benzothiazoles. Illustratively, suitable leaving groups include those having a (conjugate acid) pKa of less than 6, less than 5.5, less than 5, less than 4.5, less than 4, less than 3.5, less than 3, less than 2.5, less than 2, less than 1.5, less than 1, less than 0.5, and/or less than 0. For example, $Q^{11}$ can be a halogen atom, an alkyl sulfonate group (e.g., a triflate group, a mesylate group, etc.), an aryl sulfonate group (e.g., a tosylate group), and an acyloxy group (e.g., a acetoxy group).

As discussed above, $Q^{13}$ can be an alkyl group or an aryl group. As illustrative examples of suitable alkyl groups, there can be mentioned unsubstituted C1-C12 alkyl groups, unsubstituted C1-C8 alkyl groups, unsubstituted C1-C6 alkyl groups, unsubstituted C1-C4 alkyl groups, substituted C1-C12 alkyl groups, substituted C1-C8 alkyl groups, substituted C1-C6 alkyl groups, substituted C1-C4 alkyl groups, methyl, ethyl, n-propyl, i-propyl, n-butyl i-butyl, t-butyl, cyclohexyl, cyclopentyl, cyclohexenyl, cyclopentenyl, and the like. As illustrative examples of suitable aryl groups, there can be mentioned 5-20 membered homocyclic rings, 5-20 membered heterocyclic rings, 5-10 membered homocyclic rings, 5-10 membered heterocyclic rings, phenyl, naphthyl, pyridyl, and the like, which can be unsubstituted or substituted with, for example, one or more alkyls, alkoxys, halogens, or combinations thereof. As further illustration, $Q^{13}$ can be a moiety having the formula -$Q^5$-$Q^6$, where $Q^5$ is a C1-C12 saturated or unsaturated alkylene moiety, optionally containing one or more heteroatoms and where $Q^6$ is a substituted or unsubstituted, 5-20 membered, heterocyclic or homocyclic ring; such as in the case where -$Q^5$- is an unsaturated alkylene moiety having the formula —CH=CH—, as in the case where $Q^6$ is a substituted or unsubstituted phenyl ring, and such as in the case where -$Q^5$- is an unsaturated alkylene moiety having the formula —CH=CH— and $Q^6$ is a substituted or unsubstituted phenyl ring.

Also as discussed above, $Q^{14}$ can be a hydrogen atom, an alkyl group, or an aryl group. As illustrative examples of suitable alkyl groups, there can be mentioned unsubstituted C1-C12 alkyl groups, unsubstituted C1-C8 alkyl groups, unsubstituted C1-C6 alkyl groups, unsubstituted C1-C4 alkyl groups, substituted C1-C12 alkyl groups, substituted C1-C8 alkyl groups, substituted C1-C6 alkyl groups, substituted C1-C4 alkyl groups, methyl, ethyl, n-propyl, i-propyl, n-butyl i-butyl, t-butyl, cyclohexyl, cyclopentyl, cyclohexenyl, cyclopentenyl, and the like. As illustrative examples of suitable aryl groups, there can be mentioned 5-20 membered homocyclic rings, 5-20 membered heterocyclic rings, 5-10 membered homocyclic rings, 5-10 membered heterocyclic rings, phenyl, naphthyl, pyridyl, and the like, which can be unsubstituted or substituted with, for example, one or more alkyls, alkoxys, halogens, or combinations thereof.

Also as discussed above, $Q^{13}$ and $Q^{14}$, taken together with the carbon atoms to which they are bonded, can represent a 5-12 membered ring. The 5-12 membered ring can be homocyclic or heterocyclic, substituted or unsubstituted, monocyclic or polycyclic. Illustratively, the 5-12 membered ring can be a substituted or unsubstituted 5- or 6-membered ring (e.g., a cyclopentyl ring or a cyclohexyl ring).

In certain embodiments, the method of the present invention can be used to prepare 7-substituted indoles, for example, by using a 7-substituted-4,5-dihydro indole having the formula:

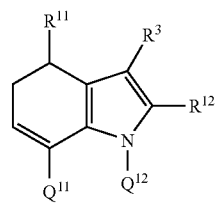

and contacting the 7-substituted-4,5-dihydro indole with the vinyldiazo compound in the presence of a dirhodium catalyst under conditions effective to produce a compound having the formula:

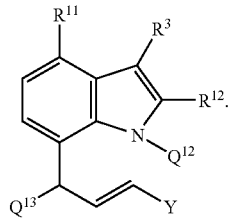

In other embodiments, the method of the present invention can be used to prepare a 7-substituted benzofuran, for example, by using a 7-substituted-4,5-dihydro benzofuran having the formula:

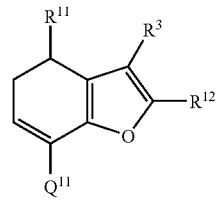

and contacting the 7-substituted-4,5-dihydro benzofuran with the vinyldiazo compound in the presence of a dirhodium catalyst under conditions effective to produce a compound having the formula:

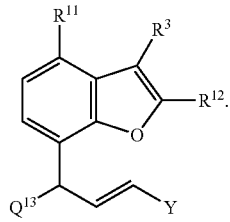

In still other embodiments, the method of the present invention can be used to prepare a 7-substituted benzothiophene, for example, by using a 7-substituted-4,5-dihydro benzothiophene having the formula:

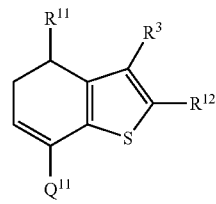

and contacting the 7-substituted-4,5-dihydro benzothiophene with the vinyldiazo compound in the presence of a dirhodium catalyst under conditions effective to produce a compound having the formula:

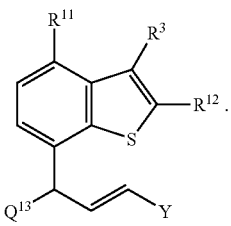

In yet other embodiments, the method of the present invention can be used to prepare a 7-substituted benzimidazole, for example, by using a 7-substituted-4,5-dihydro benzimidazole having the formula:

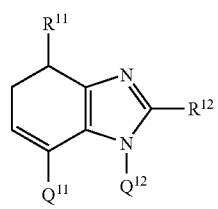

and contacting the 7-substituted-4,5-dihydro benzimidazole with the vinyldiazo compound in the presence of a dirhodium catalyst under conditions effective to produce a compound having the formula:

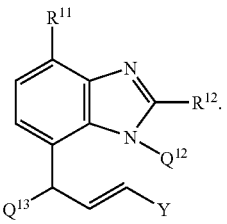

In still other embodiments, the method of the present invention can be used to prepare a 7-substituted benzoxazole, for example, by using a 7-substituted-4,5-dihydro benzoxazole having the formula:

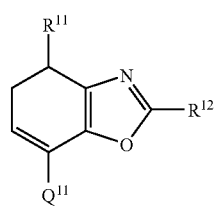

and contacting the 7-substituted-4,5-dihydro benzoxazole with the vinyldiazo compound in the presence of a dirhodium catalyst under conditions effective to produce a compound having the formula:

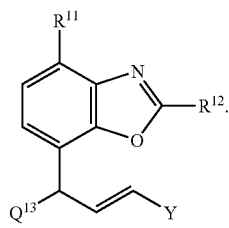

In yet other embodiments, the method of the present invention can be used to prepare a 7-substituted benzothiazole, for example, by using a 7-substituted-4,5-dihydro benzothiazole having the formula:

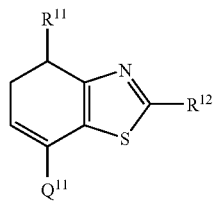

and contacting the 7-substituted-4,5-dihydro benzothiazole with the vinyldiazo compound in the presence of a dirhodium catalyst under conditions effective to produce a compound having the formula:

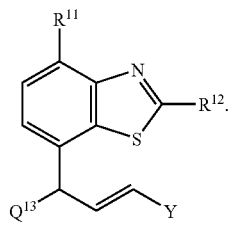

Using the methods of the present invention, compounds having the formula:

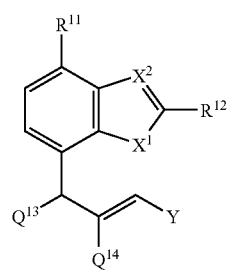

can be enriched in one or the other enantiomer, i.e., in an enantiomer having the formula:

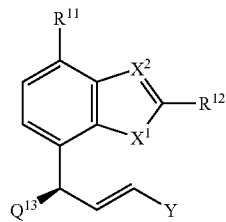

or in an enantiomer having the formula:

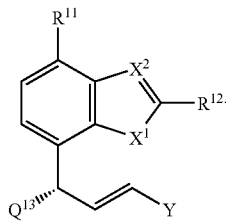

Such enantiomeric enrichment (e.g., >50% ee, >55% ee, >60% ee, >70% ee, >80% ee, >85% ee, >90% ee, >95% ee, >98% ee, and/or >99% ee) can be achieved by contacting the 7-substituted-4,5-dihydro indole, benzofuran, benzothiophene, benzimidazole, benzoxazole, or benzothiazole compound with the vinyldiazo compound in the presence of a dirhodium catalyst having $D_2$ symmetry under conditions effective to selectively produce compounds having the formula:

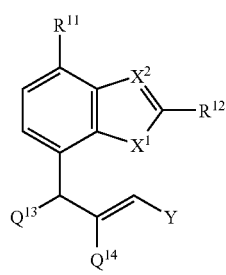

that are enriched in one or the other enantiomer.

It will be appreciated that the methods of the present invention for making 7-substituted indoles, benzofurans, benzothiophenes, benzimidazoles, benzoxazoles, or benzothiazoles can, optionally, include additional steps, for example, to convert compounds having the formula:

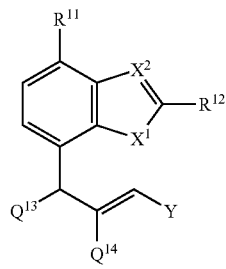

to other 7-substituted indoles, benzofurans, benzothiophenes, benzimidazoles, benzoxazoles, or benzothiazoles.

Illustratively, in the case where $X^1$ is an N-$Q^{12}$ group, where $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group, the method of the present invention can further include a step in which the N-$Q^{12}$ group is converted to an N—H group. This step can be carried out by any suitable method, such as by treating the compound in which $X^1$ is N-$Q^{12}$ with a strong acid.

As further illustration, the methods of the present invention for making 7-substituted indoles, benzofurans, benzothiophenes, benzimidazoles, benzoxazoles, or benzothiazoles can, optionally, include additional steps, for example, to convert compounds having the formula:

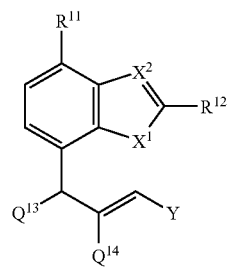

to 4-substituted indoles, benzofurans, benzothiophenes, benzimidazoles, benzoxazoles, or benzothiazoles having the formula:

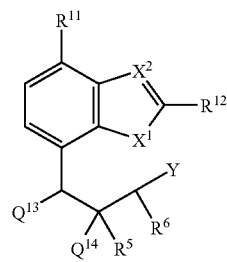

in which Y is an electron withdrawing group, a aldehyde group, or a —CH$_2$OH or other alkyl group; and in which each of $R^5$ and $R^6$ is a hydrogen atom, or in which $R^5$ and $R^6$, taken together, represent a second bond between the carbon atoms to which they are bonded. For example, in the case where Y is a carboxylic (e.g., acid, ester, etc.) electron withdrawing group, the conversion of the Y electron withdrawing group to an aldehyde group, or to a —CH$_2$OH group, or to another alkyl group, can be readily achieved, for example, by the use of a suitable reducing agent and a combination of suitable reducing agents. Additionally or alternatively, compounds in which $R^5$ and $R^6$, taken together, represent a second bond between the carbon atoms to which they are bonded can be converted to compounds in which each of $R^5$ and $R^6$ is a hydrogen atom, for example by catalytic hydrogenation.

It will be appreciated that the methods of the present invention can be used to prepare compounds having the formula:

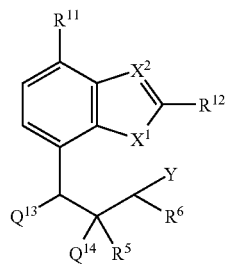

that are enriched (e.g., >50% ee, >55% ee, >60% ee, >70% ee, >80% ee, >85% ee, >90% ee, >95% ee, >98% ee, and/or >99% ee) in one or the other enantiomer, i.e., in an enantiomer having the formula:

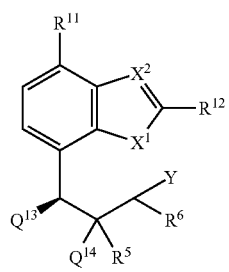

or in an enantiomer having the formula:

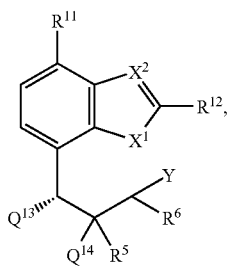

and the present invention, in another aspect thereof, relates to such compounds. In certain embodiments, in such enantiomerically enriched compounds, $R^{11}$ is a carboxylic acid group, a hydroxy group, or a thiol group. In other embodiments, $R^{11}$ is not a carboxylic acid group. In still other embodiments, $R^{11}$ is not a hydroxy group. In yet other embodiments, $R^{11}$ is not a thiol group. In still other embodiments, $R^{11}$ is not a carboxylic acid group, a hydroxy group, or a thiol group. In certain embodiments, in such enantiomerically enriched compounds, $R^{12}$ is a carboxylic acid group, a hydroxy group, or a thiol group. In other embodiments, $R^{12}$ is not a carboxylic acid group. In still other embodiments, $R^{12}$ is not a hydroxy group. In yet other embodiments, $R^{12}$ is not a thiol group. In still other embodiments, $R^{12}$ is not a carboxylic acid group, a hydroxy group, or a thiol group. In certain embodiments, in such enantiomerically enriched compounds, $R^3$ is a carboxylic acid group, a hydroxy group, or a thiol group. In other embodiments, $R^3$ is not a carboxylic acid group. In still other embodiments, $R^3$ is not a hydroxy group. In yet other embodiments, $R^3$ is not a thiol group. In still other embodiments, $R^3$ is not a carboxylic acid group, a hydroxy group, or a thiol group. In certain embodiments, in such enantiomerically enriched compounds, $R^{11}$ is not a carboxylic acid group, a hydroxy group, or a thiol group; $R^{12}$ is not a carboxylic acid group, a hydroxy group, or a thiol group; and $R^3$ is not a carboxylic acid group, a hydroxy group, or a thiol group.

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like.

"Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl".

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, indole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" refers to a homocyclic or heterocyclic ring which can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

As used herein, "dirhodium catalyst" is meant to include any material which is or can be used as a catalyst which contains two rhodium atoms and/or ions that are bonded with one another. The nature of the bond is not limitative: it can be covalent, ionic, van der Walls, pi-pi, sigma-pi, etc., or combinations of these. Of course, the dirhodium catalyst can include other atoms or ions or groups of atoms (e.g., ligands). "Dirhodium catalyst" is also meant to include dirhodium or dirhodium-containing compounds that are attached to surfaces, such as dirhodium complexes which contain one or more ligands that is or are bonded (directly or indirectly) to a surface. Illustratively, each rhodium in the dirhodium catalyst can have a formal charge of +2, and the charge on the overall complex can be neutral.

Examples of suitable dirhodium catalysts include catalysts having the formula $L_4Rh$—$RhL_4$ where each of the L's is the same or different and represents a coordinating atom from one or more ligands.

For example, the dirhodium catalyst can be a dirhodium tetracarboxylate catalyst (i.e., a catalyst having the formula $L_4Rh$—$RhL_4$ where each of the L's represents a carboxylate oxygen from one of four carboxylate groups.

Examples of dirhodium tetracarboxylate catalysts include dirhodium acetate dimer, dirhodium propionate dimer, dirhodium butyrate dimer, dirhodium pentanoate dimer, dirhodium hexanoate dimer, dirhodium heptanoate dimer, dirhodium octanoate dimer, fluorinated analogs thereof (e.g. dirhodium heptafluorobutyrate dimer), and combinations thereof.

Other illustrative examples of dirhodium tetracarboxylate catalysts include those having the formula ("Formula I"):

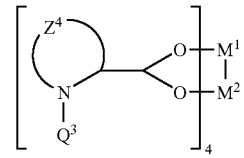

In Formula I, each of $M^1$ and $M^2$ is Rh. $Z^4$ represents the atoms necessary to complete a 3-12 membered heterocyclic ring, such as an alkylene moiety (e.g., a —$CH_2CH_2CH_2$— moiety). $Q^3$ is an electron withdrawing group, such as a group having the formulae —$C(O)R^9$, —$SO_2R^9$, or —$P(O)R^9R^{9'}$, where each of $R^9$ and $R^{9'}$ is independently selected from an alkyl group, an aryl group, and an alkoxy group.

As used herein, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion*, New York: John Wiley & Sons, pp. 145-147 (1972) ("Gordon"), which is hereby incorporated by reference. Suitable electron-withdrawing groups include those having a para value higher than or equal to about 0.2 or higher than or equal to about 0.3, with reference to the Hammett scale. Illustratively, suitable electron withdrawing groups include esters, amides, ketones, phosphonates, sulfonates, sulfones, nitro, trifluoromethyl groups and other perfluoronated alkyl groups, and the like. Particular examples of electron withdrawing groups are moieties having the formulae —C(O)R, —SO$_2$R, and —P(O)RR', where R and R' are independently selected from an alkyl group, an aryl group, and an alkoxy group.

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e., —CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

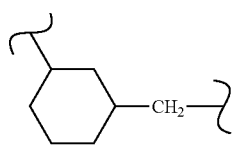

In Formula I and in all other formulae set forth in this document which contain one or more chiral centers and which do not specify the stereochemistry of a particular chiral center, such formulae are to be construed as encompassing all possible stereochemistries. Thus, for example, Formula I is meant to include (i) compounds in which the unspecified chiral center is entirely in the R configuration, (ii) compounds in which the unspecified chiral center is entirely in the S configuration, and (iii) racemic and other mixtures of (i) and (ii).

Illustratively, dirhodium tetracarboxylate catalysts of Formula I are meant to include substantially chirally pure catalysts having one of the following formulae ("Formula II-A" and "Formula II-B", respectively):

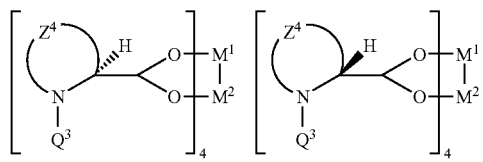

as well as dirhodium tetracarboxylate catalysts of Formula I having D$_2$ symmetry. Molecules having D$_2$ symmetry are molecules which have a vertical C$_2$ axis and a set of two C$_2$ axes perpendicular to the vertical C$_2$ axis. D$_2$ symmetry is further described in, for example, Cotton et al., *Advanced Inorganic Chemistry*, 4th ed., New York: John Wiley & Sons, pages 28-46 (1980), which is hereby incorporated by reference.

Specific examples of suitable catalysts having Formulae I and II include: Rh$_2$(DOSP)$_4$, Rh$_2$(S-DOSP)$_4$, and Rh$_2$(R-DOSP)$_4$, which are compounds having Formulae I, II-A, and II-B, respectively, in which each of M$^1$ and M$^2$ is Rh, Z$^4$ is a —CH$_2$CH$_2$CH$_2$— group, and Q$^3$ represents a 4-dodecylphenylsulfonyl moiety; and Rh$_2$ (TBSP)$_4$, Rh$_2$(S-TBSP)$_4$, and Rh$_2$(R-TBSP)$_4$, which are compounds having Formulae I, II-A, and II-B, respectively, in which each of M$^1$ and M$^2$ is Rh, Z$^4$ is a —CH$_2$CH$_2$CH$_2$— group, and Q$^3$ represents a 4-t-butylphenylsulfonyl moiety. These and other illustrative compounds having Formulae I, II-A, and II-B are described in greater detail in Davies, "Rhodium-Stabilized Vinylcarbenoid Intermediates in Organic Synthesis," *Current Organic Chemistry*, 2:463-488 (1998), which is hereby incorporated by reference.

Other suitable dirhodium tetracarboxylate catalysts include those which contain two rhodium atoms or ions that are bonded to one another along an axis. This can be represented by the formula Rh—Rh, where the dash represents the bond and the bond axis. These catalysts also contain two carboxylate ligands. As used herein, "carboxylate ligands" means ligands which contain one or more carboxylate groups. As used herein, carboxylate groups mean groups having the formula:

which can be written with the following formula:

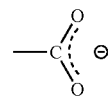

where the dashed line represents the delocalized electrons. Alternatively, the carboxylate group can be expressed without showing the delocalized electrons, as in the following formula:

Each of the two carboxylate ligands includes two carboxylate groups, and these two carboxylate groups are bonded to each other via a moiety having the formula ("Formula III"):

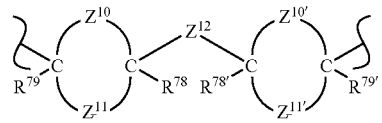

In Formula III, $Z^{10}$ and $Z^{11}$, together with the atoms to which they are bonded form a 3-12 membered ring, and $Z^{10'}$ and $Z^{11'}$, together with the atoms to which they are bonded form a 3-12 membered ring. $Z^{10}$ and $Z^{10'}$ can be the same, and each can contain a heteroatom, such as a nitrogen, oxygen, or sulfur. For example in one embodiment, $Z^{10}$ and $Z^{10'}$ are the same, and each represents a single heteroatom selected from the group consisting a sulfur atom, an oxygen atom, and an optionally substituted nitrogen atom. In another illustrative embodiment, at least one of $Z^{10}$ and $Z^{10'}$ has the formula —NQ-, at least one of $Z^{11}$ and $Z^{11'}$ is an arylene or alkylene group, and Q is an electron withdrawing group. In yet another illustrative embodiment, each of $Z^{10}$ and $Z^{10'}$ has the formula —NQ-, each of $Z^{11}$ and $Z^{11'}$ is an alkylene group, and Q is an electron withdrawing group. Although one of $Z^{10}$ and $Z^{11}$ and/or one of $Z^{10'}$ and $Z^{11'}$ can represent a direct bond between the carbons to which they are attached, this need not be the case, for example as when only three, only two, only one, or none of $Z^{10}$, $Z^{11}$, $Z^{10'}$, and $Z^{11'}$ represents such a direct bond. $R^{78}$, $R^{78'}$, $R^{79}$, and $R^{79'}$ are independently selected from the group consisting of H, an alkyl group, and an aryl group, such as in the case where each of $R^{78}$, $R^{78'}$, $R^{79}$, and $R^{79'}$ represents a hydrogen. $Z^{12}$ represents an alkylene or arylene group, such as a substituted or unsubstituted 1,3-phenylene group.

As indicated in the formulae above, each of the two carboxylate groups includes a first carboxylate oxygen atom ("$O^1$"), a second carboxylate oxygen atom ("$O^2$"), and a carbon ("C") to which the $O^1$ and the $O^2$ are bonded thereby forming two $O^1$—C—$O^2$ moieties. $O^1$ of each of the two carboxylate groups of each of the two carboxylate ligands is bonded to the first rhodium ($Rh^1$); $O^2$ of each of the two carboxylate groups of each of the two carboxylate ligands is bonded to the second rhodium ($Rh^2$).

Each of the two carboxylate ligands further includes at least two stereocenters. These stereocenters, for example, can be included in one or more of $Z^{10}$, $Z^{11}$, $Z^{10'}$, and $Z^{11'}$, and/or they can be located at the carbon atoms to which $Z^{10}$, $Z^{11}$, $Z^{10'}$, and $Z^{11'}$ are bonded. The stereochemistry at these stereocenters are selected such that the catalyst, taken as a whole, has $D_2$ symmetry.

Illustrative examples of such dirhodium tetracarboxylate catalysts include those having the formula ("Formula IV"):

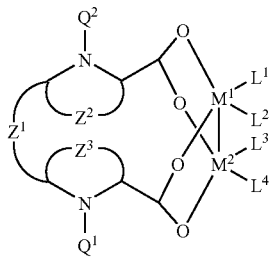

In Formula IV, $M^1$ and $M^2$ represent rhodium atoms or ions. $Z^2$ and $Z^3$, independently, are the atoms necessary to complete a 3-12 membered heterocyclic ring. Examples of such atoms include: substituted or unsubstituted alkylene moieties, such as those having the formula —$(CH_2)_i$—, where i is an integer from 1 to 8; and moieties having the formula —$(CH_2)_i$—X—$(CH_2)_j$—, where i and j each independently represent integers from 0 to 4 and X is a heteroatom, such as O, S, and $NR^{70}$, where $R^{70}$ is a substituted or unsubstituted alkyl, aryl, or heteroaryl group. Illustratively, $Z^2$ and $Z^3$ can be the same, as in the case where each of $Z^2$ and $Z^3$ has the formula —$CH_2CH_2$—. $Z^1$ is an alkylene or arylene group. Illustratively, $Z^1$ can have the formula —$(CH_2)_i$—, where i is an integer from 1 to 8. Alternatively, $Z^1$ can have the formula —$(CH_2)_i$—X—$(CH_2)_j$—, where i and j each independently represent integers from 0 to 4 and X is a heteroatom, such as O, S, and $NR^{70}$, where $R^{70}$ is an alkyl or aryl group. Still alternatively, $Z^1$ can be a cycloalkyl moiety, such as cyclopent-1,3-diyl and cyclohex-1,3-diyl, which can be substituted or unsubstituted. Still alternatively, $Z^1$ can be an arylene moiety, such as a 1,3-phenylene or 1,3-naphthylene, or an heterocyclic moiety, such as a pyrid-3,5-diyl, pyrid-2,6-diyl, 2H-pyran-3,5-diyl, and tetrohydropyran-3,5-diyl moiety. $Q^1$ and $Q^2$ are the same or different and are electron withdrawing groups. Examples of $Q^1$ suitable for use in the practice of the present invention are moieties having the formulae —C(O)$R^1$, —$SO_2R^1$, and —P(O)$R^1R^{1'}$, and examples of suitable $Q^2$ include moieties having the formulae —C(O)$R^2$, —$SO_2R^2$, and —P(O)$R^2R^{2'}$. In these formulae, each of $R^1$, $R^{1'}$, $R^2$, and $R^{2'}$ is independently selected from an alkyl group, an aryl group, and an alkoxy group. In one illustrative embodiment, $Q^1$ has the formula —$SO_2R^1$; $Q^2$ has the formula —$SO_2R^2$; and $R^1$ and $R^2$ are the same or different and are substituted or unsubstituted alkyl or aryl groups, such as in the case where $Q^1$ has the formula —$SO_2R^1$; $Q^2$ has the formula —$SO_2R^2$; and each of $R^1$ and $R^2$ is independently selected from the group consisting of 4-(t-butyl)phenyl, 2,4,6-trimethylphenyl, and 2,4,6-triisopropylphenyl. In the above Formula IV, $L^1$ and $L^3$, taken together, represent a —O—$CR^{13}$—O— moiety, and $L^2$ and $L^4$, taken together, represent a —O—$CR^{14}$—O— moiety. In these moieties, $R^{13}$ and $R^{14}$ can be the same or they can be different, and each is independently selected from the group consisting of alkyl groups and aryl groups. Alternatively, $R^{13}$ and $R^{14}$ can represent alkylene or arylene groups that are directly or indirectly bonded to one another. In the latter case, the dirhodium tetracarboxylate catalysts of Formula IV can be expressed as the following formula ("Formula V"):

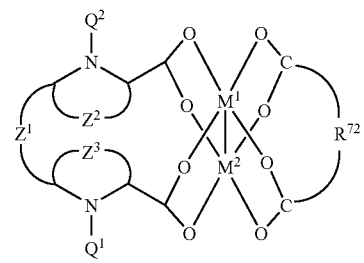

where $R^{72}$ represents an alkylene or arylene group. Illustratively, $R^{72}$ can be selected such that the dirhodium tetracarboxylate catalysts of Formula V have the following formula ("Formula VI"):

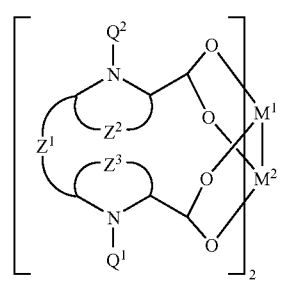

The dirhodium tetracarboxylate catalysts of Formulae IV, V, and VI have at least four stereocenters (i.e., at least the two carbons to which $Z^2$ is bonded and at least the two carbons to which $Z^3$ is bonded are stereocenters). Formulae IV, V, and VI are not meant to be limited to any particular set of configurations at the catalyst's stereocenters, and the structures given in these formulae are meant to be broadly read to include any and all possible collections of stereocenters. For example, catalysts of Formula VI are meant to include (i) compounds having the formula ("Formula VII"):

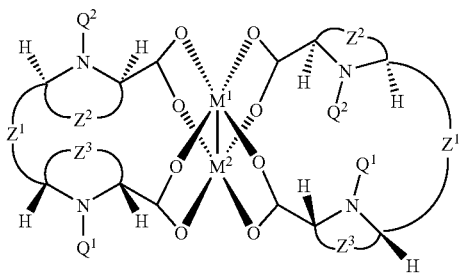

and (ii) compounds having the formula ("Formula VIII"):

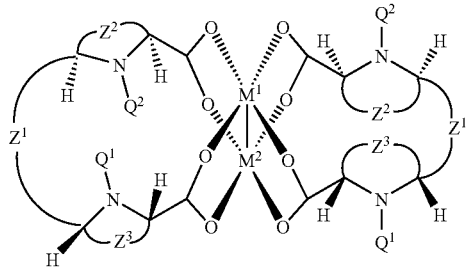

Each of the catalysts having Formulae VII and VIII can be present alone (i.e., as a pure diastereoisomer), or it can be present in a mixture with one or more different diastereoisomers. Alternatively, the catalysts having Formulae VII and VIII can be substantially free of other diastereoisomers. In this context, "substantially free of other diastereoisomers" means that the molar ratio of other diastereoisomers to the catalyst is less than 40%, such as less than 30%, less than 20%, less than 10%, less than 5%, less than 2%, and/or less than 1%.

Examples of catalysts having Formula VII and VIII, respectively, are those having the formula ("Formula IX"):

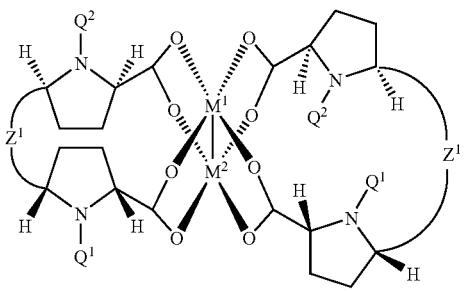

and those having the formula ("Formula X"):

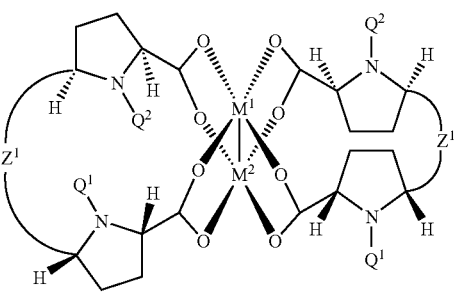

Still other examples of catalysts having Formula VII and VIII, respectively, are those having the formula ("Formula XI"):

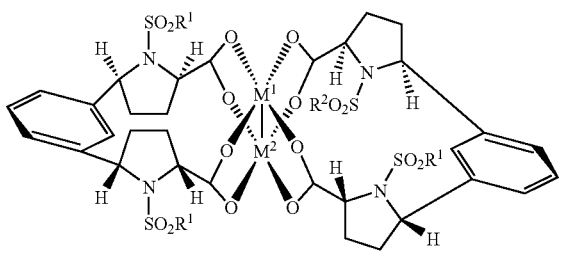

and those having the formula ("Formula XII"):

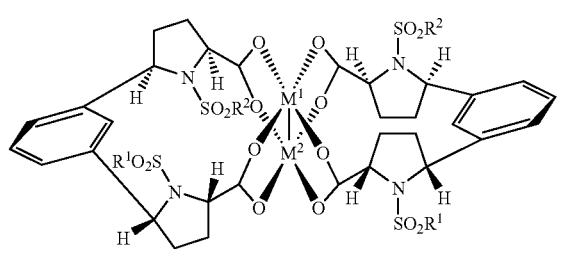

In Formula XI and Formula XII, $R^1$ and $R^2$ can be the same or different and each can be selected from, for example, alkyl groups and aryl groups.

As used in the above discussion and elsewhere herein, "arylene" is meant to include a bivalent aryl group in which both valencies are present on aromatic carbons. Examples of such groups include, for example, 1,3-phenylene, 1,4-phenylene, 5-methyl-1,3-phenylene, pyrid-2,3-diyl, pyrid-2,4-diyl, pyrid-2,5-diyl, pyrid-3,5-diyl, 1,3-naphthylene, 1,7-naphthylene, 1,8-naphthylene, 5,6,7,8-tetrahydro-1,3-naphthylene, thiophene-2,5-diyl, and furan-2,5-diyl. "Arylene", as used herein, is also meant to include a bivalent group having the formula —R—R'—, where R is an alkyl group and R' is an aryl group. As the structure of —R—R'— indicates, one of the valencies is on the R (i.e., alkyl) portion of the —R—R'— moiety and the other of the valencies resides on the R' (i.e., aryl) portion of the —R—R'— moiety. Examples of this type of arylene moiety include moieties having the formulae:

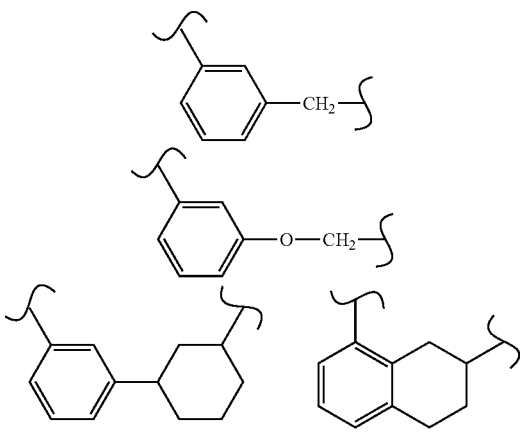

and the like.

Other suitable dirhodium tetracarboxylate catalysts as well as methods for making various dirhodium tetracarboxylate catalysts are described in, for example, U.S. Pat. No. 6,410,746 to Davies, International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287-5290 (1999), each of which is hereby incorporated by reference.

Other suitable dirhodium catalysts include dirhodium tetracarboxamidate catalysts, such as those having the following formula ("Formula XIII"):

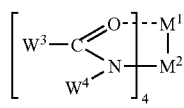

In Formula XIII, each of $M^1$ and $M^2$ is Rh. $W^3$ represents an alkyl group, an aryl group, an alkoxy group, or an amine group, and $W^4$ represents an alkyl group or an aryl group. Alternatively, $W^3$ and $W^4$, taken together with the atoms to which they are bonded, represent a 3-12 membered ring, for example, as shown in the following formula ("Formula XIV"):

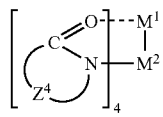

In Formula XIV, $Z^4$ represents the atoms necessary to complete a 3-12 membered ring. The ring can be substituted or unsubstituted; and it can include additional heteroatoms (i.e., in addition to the N to which $Z^4$ is bonded, or it can consist only of carbons (except for the N to which $Z^4$ is bonded). Illustratively, $Z^4$, together with the carbon and N atoms to which it is bonded, can represents a substituted or unsubstituted C3-C8 lactam ring, a substituted or unsubstituted oxazolidone ring, a substituted or unsubstituted pyrrolidone ring, or a substituted or unsubstituted imidazolidone ring. Specific examples of suitable catalysts of Formula XIV include: dirhodium(II) tetrakis(caprolactam); dirhodium(II) tetrakis[methyl 2-oxazolidone-4-carboxylate]; dirhodium (II) tetrakis[methyl 2-oxazolidone-4-(S)-carboxylate]; dirhodium(II) tetrakis[methyl 2-pyrrolidone-5-carboxylate]; dirhodium(II) tetrakis[methyl 2-pyrrolidone-5(R)-carboxylate]; dirhodium(II) tetrakis(methyl 2-pyrrolidone-5(S)-carboxylate]; dirhodium(II) tetrakis[methyl 1-(3-phenylpropanoyl)-2-imidazolidone-4-carboxylate; dirhodium(II) tetrakis[methyl 1-(3-phenylpropanoyl)-2-imidazolidone-4 (S)-carboxylate; and adducts (e.g., acetonitrile and/or alcohol adducts) thereof. Methods for producing these and other dirhodium tetracarboxamidate catalysts can be found, for example, in U.S. Pat. No. 5,175,311 to Doyle, which is hereby incorporated by reference.

The aforementioned dirhodium catalysts can be tethered, for example as described in WO 03/018184, which is hereby incorporated by reference. Additionally, the aforementioned dirhodium catalysts can be used in conjunction with an organic ester, as described in WO 03/018183, which is hereby incorporated by reference.

As used herein, "alkylcarbonyl", is meant to refer to a group having the formula —C(O)—R, where R is an alkyl group. As used herein, "arylcarbonyl" is meant to refer to a group having the formula —C(O)—R, where R is an aryl group. As used herein, "alkyloxycarbonyl" is meant to refer to a group having the formula —C(O)—O—R, where R is an alkyl group. As used herein, "aryloxycarbonyl" is meant to refer to a group having the formula —C(O)—O—R, where R is an aryl group.

The present invention is further illustrated by the following non-limiting examples.

EXAMPLES

Example 1

Enantioselective Synthesis of 4-Substituted Indoles and Benzothiophenes

Scheme 1 sets forth a strategy for enantioselectively synthesizing 4-substituted indoles 2 from a 4-acetoxy-6,7-dihydroindole (1) via a rhodium(II)-catalyzed combined C—H activation/Cope rearrangement-elimination reaction:

SCHEME 1

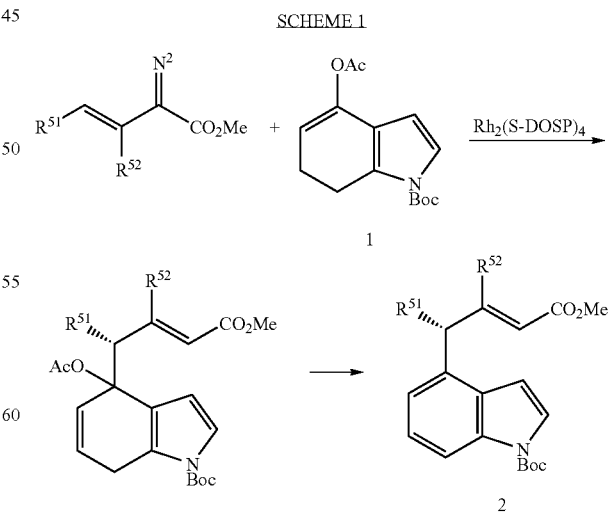

Initially, we were interested in exploring dirhodium catalyzed reaction of vinyl diazo compounds with 4-acetoxy-6, 7-dihydroindole. While the pyrrole component contained within 4-acetoxy-6,7-dihydroindole could be susceptible to a [4+3] cycloaddition with rhodium stabilized vinylcarbenoids, the system could also be susceptible to C—H activation, and it was intriguing to determine what type of reactivity would be exhibited by this system. The product of the reaction turned out to be a 4-substituted indole, and, furthermore, the enantioselectivity of the reaction was found to be high. The reaction was optimized, and the results are shown in Table 1.

TABLE 1

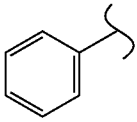

| diazo:substrate molar ratio | solvent | temp (° C.) | % yield | % ee |
| --- | --- | --- | --- | --- |
| 1.2:1 | hexane/toluene | 23 | 64 | 97.8 |
| 1:1.2 | hexane/toluene | 23 | 56 | 97.7 |
| 1.3:1 | trifluorotoluene | 23 | 39 | 94.5 |
| 1.3:1 | 2,2-dimethylbutane | 23 | 65 | 98.5 |
| 1.5:1 | 2,2-dimethylbutane | 0 | 58 | 98.8 |
| 1.5:1 | 2,2-dimethylbutane | 23 | 60 | 97.7 |

After identifying optimum reaction conditions, the reaction was explored using different diazo compounds. Some examples illustrating the scope of the reaction are outlined in Table 2.

TABLE 2

| table entry | compound | R53 | % yield | % ee |
| --- | --- | --- | --- | --- |
| 1 | a | Ph-CH2- | 65 | 98.5 |
| 2 | b | 4-MeO-C6H4- | 52 | 98.0 |
| 3 | c | 4-Br-C6H4- | 53 | 98.7 |
| 4 | d | 3,4-Cl2-C6H3- | 45 | 98.0 |
| 5 | e | 2-naphthyl | 56 | 98.0 |
| 6 | f | 3-indolyl(N-Boc) | 64 | 97.7 |
| 7 | g | PhCH=CH- | 56 | 99.0 |
| 8 | h | CH3- | 61 | 98.6 |

The $Rh_2(S\text{-}DOSP)_4$-catalyzed reaction with 4-acetoxy-6,7-dihydroindole (1) is applicable to a range of terminally-substituted vinyldiazoacetates 3, as illustrated in Tables 1 and 2. For the syntheses described in Table 2, the standard reaction conditions used 1 mol % of catalyst and 2,2-dimethylbutane ("DMB") as solvent. Electron-rich and electron-deficient aryl substituents are compatible with this chemistry (entries 1-5 in Table 2), as well as an indolylvinyldiazoacetate (entry 6 in Table 2). A dienyldiazoacetate is equally effective (entry 7 in Table 2) and even an alkyl substituent can be accommodated (entry 8 in Table 2). In all instances the new stereogenic centers in the 4-substituted indoles 4 are formed in >97% ee. The absolute configuration of the bromophenyl derivative 4c (entry 3 in Table 2) was determined by X-ray crystallography of the reduced analogue (and the X-ray crystallographic data have been submitted to the Cambridge Structure Database (Nygren et al., *Private Communication* CCDC 279134 (2005), which is hereby incorporated by reference), while the absolute configurations of other derivates have been tentatively assigned assuming an analogous enantioinduction. The yields in these reactions ranged from 45-65% because there was some competing reaction initiated at the pyrrole ring (Davies, et al., *J. Org. Chem.*, 62:1095-1105 (1997), which is hereby incorporated by reference).

4-Substituted indoles can also be formed in the reaction of cyclic vinyldiazoacetates 5, as illustrated in the following Scheme 2.

SCHEME 2

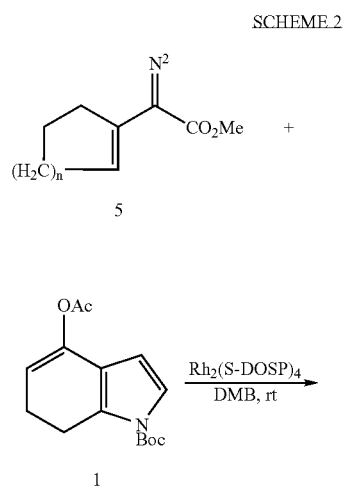

In these cases, competing reactions on the pyrrole ring were not observed and the 4-substituted indoles 6a (n=1) and 6b (n=2) were formed in 95% and 90% yields, respectively. Once, again, the enantioselectivities in these reactions were very high (6a: 98.8% ee and 6b: 94% ee).

The C—H activation was extended to a 4-substituted 6,7-dihydrobenzothiophene 7 as illustrated in Scheme 3. Thiophenes are common reaction partners with rhodium carbenoids (Padwa et al., *J. Org. Chem.*, 54:299-308 (1989), which is hereby incorporated by reference). However, in this case, the C—H activation is the dominant reaction, generating the 4-substituted benzothiophene 8 in 89% yield and 99% ee.

SCHEME 3

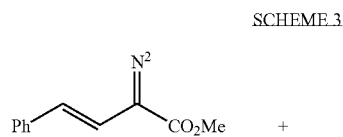

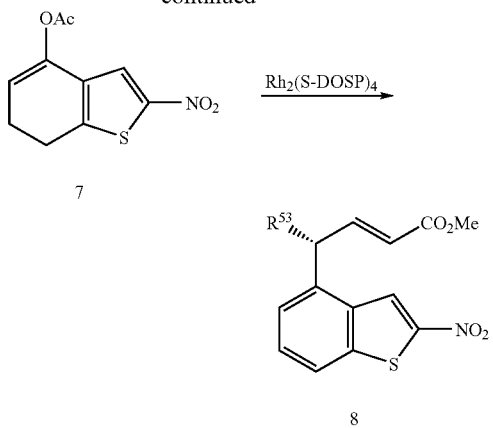

The C—H activation strategy to prepare 4-substituted indoles compliments some of the more conventional methods for indole synthesis as illustrated in Scheme 4.

SCHEME 4

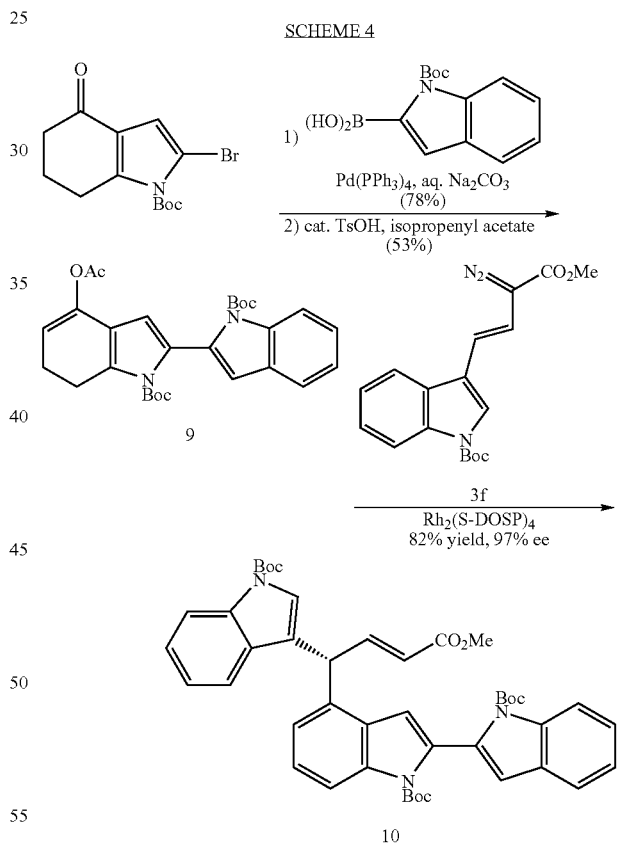

Palladium catalyzed coupling (Thoresen, et al., *Synlett*, 1998: 1276-1278 (1998), which is hereby incorporated by reference) followed by acylation (Maekawa et al., *Chirality*, 15:95-100 (2003) ("Maekawa"), which is hereby incorporated by reference) readily forms the 2-indole derivative 9. Rh$_2$(S-DOSP)$_4$, catalyzed reaction of 9 with the 3-indolylvinyldiazoacetate 3f generates the trisindole derivative 10 in 82% yield and 97% ee. In 10, one indole is 2-substituted, another is 3-substituted, and the third is 2,4-disubstituted. The successful outcome of this reaction underscores the facility of the combined C—H activation/Cope rearrangement because indoles have often been shown to be reactive partners in carbenoid chemistry (Davies pp. 1-18 in *Advances in Nitrogen Heterocycles*, Vol. 1, Moody, ed., London:JAI Press (1995), which is hereby incorporated by reference).

As noted above, using the described methodology, the desired indole can be formed in good yield, even thought the precursor contains a 2,3-unsubstituted pyrrole ring (a moiety known to be reactive toward cyclopropanation under the reaction conditions. It is believed that the apparent favorability of the combined C—H activation/Cope rearrangement reaction and the electronically deactivating BOC protecting group on the pyrrole ring may be responsible for this surprising selectivity. Indeed, the major by-product of this reaction results from a tandem cyclopropanation/Cope rearrangement of the pyrrole ring to yield a very unusual tropane structure, as shown below:

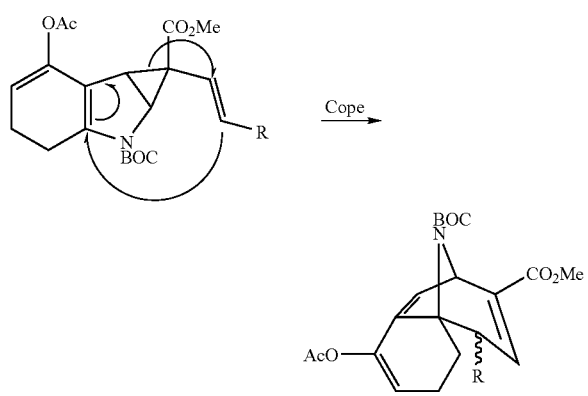

In order to minimize tropane formation, it was envisioned that induction of a substituent at either the 2 or 3 position of the pyrrole ring would effectively block this alternate reaction pathway and lead exclusively to the formation of the indole because trisubstituted alkenes are poor substrates for cyclopropanation under these conditions. For example, this strategy was employed in Scheme 3 where a nitro group was used at the 2 position to protect against cyclopropanation and improve yield of the desired 4-substituted benzothiophene product.

A number of potential applications of this chemistry to the synthesis of pharmaceutical targets can be envisioned. The resulting 2,4-disubstituted indole would be expected to be functionalized by standard electrophilic substitution methodologies or even cyclized under Friedel-Crafts conditions to give a 3,4-bridging 7-membered ring. This scaffold can potentially be used for entry into the ergot and hapalindole series of alkaloids, for example, as illustrated below:

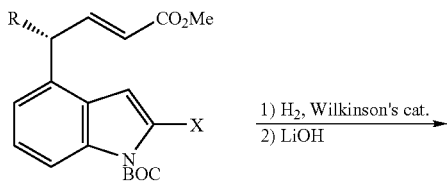

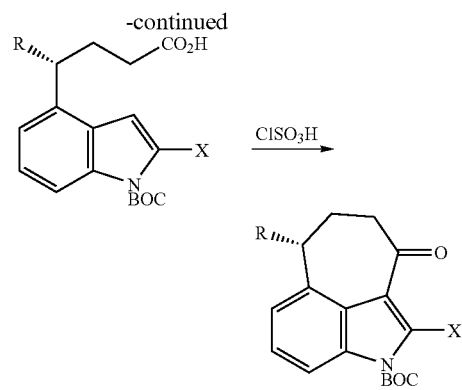

where X can be H, Ar, or Me.

Example 2

Synthesis of tert-butyl 4,5,6,7-tetrahydro-4-oxoindole-1-carboxylate

Tert-butyl 4,5,6,7-tetrahydro-4-oxoindole-1-carboxylate:

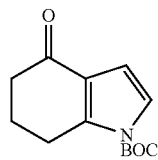

was prepared using a modified literature procedure (Basel et al., *Synthesis*, 4:550-552 (2001) ("Basel"), which is hereby incorporated by reference). To a flame-dried 250 mL round bottom flask under argon and charged with a stir bar was added 1,5,6,7-tetrahydro-4H-indol-4-one (4.8 g, 35.5 mmole), di-tert-butyl dicarbonate (8.4 g, 38.6 mmole), and 150 mL dry acetonitrile. DMAP (43 mg, 0.36 mmole) was then added and the solution stirred overnight at ambient temperature. Imidazole (0.48 g, 7.1 mmole) was then added, and the solution stirred for an additional 15 minutes. Chloroform (250 mL) was then added and the mixture washed with 0.5% HCl solution (3×200 mL). The organic layer was then dried over anhydrous $MgSO_4$, filtered through a plug of silica gel, and concentrated in vacuo to give pure product as a white solid (8.1 g, 97% yield). $R_f$ 0.24 (1:1 pentane:diethyl ether); $^1$H NMR (400 MHz, $CDCl_3$) δ 7.16 (d, J=3.4 Hz, 1H), 6.55 (d, J=3.4 Hz, 1H), 3.13 (t, J=6.0 Hz, 2H), 2.48 (m, 2H), 2.15 (m, 2H), 1.61 (s, 9H).

Example 3

Synthesis of tert-butyl 4,5,6,7-tetrahydro-4-oxoindole-1-carboxylate

Tert-butyl 4,5,6,7-tetrahydro-4-oxoindole-1-carboxylate 4,5,6,7-tetrahydro-4-oxoindole-1-carboxylate (1) was prepared using a modified literature procedure (Maekawa, which is hereby incorporated by reference). To a dry 250 mL round bottom flask charged with a magnetic stir bar was added tert-butyl 4,5,6,7-tetrahydro-4-oxoindole-1-carboxylate (4.619 g, 19.6 mmole), 150 mL isopropenyl acetate and p-toluenesulfonic acid monohydrate (67 mg, 0.35 mmole).

The solution was refluxed for 5 hours while the solvent was slowly distilled off at the rate of 20 mL/hour. After cooling the solution to ambient temperature, 100 mL of a 1:1 solution of diethyl ether and saturated aqueous NaHCO$_3$ was added. The layers were separated and the aqueous layer extracted with 30 mL diethyl ether. The combined ether extracts were washed with saturated aqueous NaHCO$_3$ (2×30 mL), brine (30 mL), and dried over anhydrous MgSO$_4$. The solution was then filtered through a plug of silica gel and concentrated in vacuo. The residue was purified via flash chromatography (silica gel, 5:1 pentane:diethyl ether) to give the product as a white solid (1.40 g, 26% yield), mp 79-80° C.; R$_f$ 0.26 (5:1 pentane: diethyl ether); FTIR (neat): 2978, 1736 cm$^{-1}$; $^1$H NMR (500 MHz, CDCl$_3$) δ 7.09 (d, J=3.5 Hz, 1H), 5.95 (d, J=3.5 Hz, 1H), 5.24 (t, J=4.5 Hz, 1H), 3.10 (t, J=9.5 Hz, 2H), 2.56 (dt, J=9.5, 4.5 Hz, 2H), 2.23 (s, 3H), 1.58 (s, 9H); $^{13}$C NMR (75 MHz, CDCl$_3$) δ 169.1 (C), 149.0 (C), 143.3 (C), 130.8 (C), 119.9 (CH), 118.9 (C), 106.8 (CH), 105.4 (CH), 83.8 (C), 27.9 (CH$_3$), 23.1 (CH$_2$), 21.7 (CH$_2$), 20.7 (CH$_3$); LCMS (ESI) m/z (relative intensity): 250.0 (100), 236.0 (90); HRMS (EI) Calcd for C$_{15}$H$_{19}$NO$_4$ 277.1309, Found 277.1309.

Example 4

Synthesis of 2-bromo-6,7-dihydro-1H-indol-4(5H)-one

2-Bromo-6,7-dihydro-1H-indol-4(5H)-one:

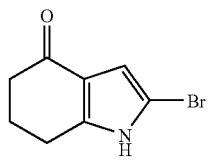

was prepared using a literature procedure (Remers et al., J. Org. Chem., 36:1241-1247 (1971) ("Remers"), which is hereby incorporated by reference). To a 100 mL round bottom flask charged with a magnetic stir bar was added 1,5,6,7-tetrahydro-4H-indol-4-one (1.2 g, 8.8 mmole) and dry THF (20 mL). Stirring was commenced, and a solution of phenyltrimethylammonium tribromide (3.33 g, 8.8 mmole) in 15 mL of dry THF was added dropwise over 10 minutes at ambient temperature. After the addition was complete, the reaction mixture was stirred for an additional 2 hours and then filtered to remove the precipitate. The filtrate was concentrated in vacuo and the residue treated with dichloromethane (30 mL) and 5% aqueous Na$_2$CO$_3$ solution (30 mL). The layers were separated and the dichloromethane layer was then washed with brine (30 mL), dried over anhydrous MgSO$_4$, filtered and concentrated in vacuo to give the crude product as a white solid which was directly used without further purification. $^1$H NMR data matched the literature values exactly ("Remers", which is hereby incorporated by reference).

Example 5

Synthesis of tert-butyl 2-bromo-4,5,6,7-tetrahydro-4-oxoindole-1-carboxylate

Tert-butyl 2-bromo-4,5,6,7-tetrahydro-4-oxoindole-1-carboxylate:

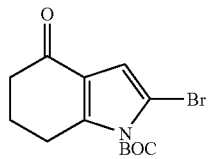

was prepared using a modified literature procedure (Basel, which is hereby incorporated by reference). To a flame-dried 250 mL round bottom flask under argon and charged with a stir bar was added crude 2-bromo-6,7-dihydro-1H-indol-4 (5H)-one (1.2 g, 8.8 mmole), di-tert-butyldicarbonate (1.92 g, 8.8 mmole), and 70 mL of dry acetonitrile. Stirring was commenced and DMAP (10 mg, 0.08 mmole) was added in one portion. The solution was stirred at ambient temperature for 1 hour, and then imidazole (0.11 g, 1.6 mmole) was added. The reaction mixture was stirred for an additional 15 minutes and the chloroform (100 mL) was added. The solution was then washed with 0.5% aqueous HCl solution (3×100 mL). The chloroform layer was then dried over anhydrous MgSO$_4$, filtered through a plug of silica gel, and concentrated in vacuo to give a brown oil. Purification by flash chromatography (silica gel, 4:1-2:1 pentane:diethyl ether) gave the product as a white solid (1.47 g, 53% yield for 2 steps). R$_f$ 0.17 (2:1 pentane:diethyl ether); FTIR (neat): 1753, 1672 cm$^{-1}$; $^1$H NMR (400 MHz, CDCl$_3$) δ 6.66 (s, 1H), 3.03 (t, J=6.0 Hz, 2H), 2.47 (m, 2H), 2.14 (m, 2H), 1.65 (s, 9H); $^{13}$C NMR (75 MHz, CDCl$_3$) δ 192.8 (C), 147.3 (C), 145.8 (C), 122.9 (C), 112.0 (CH), 102.2 (C), 86.1 (C), 36.9 (CH$_2$), 27.5 (CH$_3$), 24.6 (CH$_2$), 23.0 (CH$_2$).

Example 6

Procedures for C—H/Cope-Elimination to Form Indoles and Benzothiophenes

The following procedure is typical for all of the C—H activation reactions to synthesize 4-substituted indoles. To a flame-dried 50 mL round bottom flask under argon and charged with a magnetic stir bar was added tert-butyl 4-acetoxy-6,7-dihydroindole-1-carboxylate (0.140 g, 0.5 mmole), Rh$_2$(S-DOSP)$_4$ (9.4 mg, 0.005 mmole), and 10 mL of degassed 2,2-dimethylbutane. A solution of diazoacetate (0.65 mmole) in 5 mL of degassed 2,2-dimethylbutane and 5 mL anhydrous α,α,α-trifluorotoluene was then added with stirring at ambient temperature via syringe pump over 30 minutes. The solvent was then removed in vacuo and the residue purified by flash chromatography to give the product.

Tert-butyl 4-((S,E)-3-(methoxycarbonyl)-1-phenylallyl)-1H-indole-1-carboxylate (4a) was prepared using the general procedure set forth above. The product was purified via flash chromatography (silica gel, 7:1 pentane:diethyl ether) to give the product as a white oily solid (0.126 g, 65% yield). R$_f$ 0.26 (5:1 pentane: diethyl ether); [α]$_D^{25}$+21.0° (c 0.82, CHCl$_3$); FTIR (neat) 1720 cm$^{-1}$; $^1$H NMR (400 MHz, CDCl$_3$) δ 8.09 (d, J=8.1 Hz, 1H), 7.54-7.49 (m, 2H), 7.31-7.17 (m, 6H), 7.02 (d, J=7.3 Hz, 1H), 6.43 (d, J=3.7 Hz, 1H), 5.72 (dd, J=15.7, 1.5 Hz, 1H), 5.24 (d, J=6.6 Hz, 1H), 3.72 (s, 3H), 1.66 (s, 9H); $^{13}$C NMR (75 MHz, CDCl$_3$) δ 166.8 (C), 149.6 (CH), 141.0 (C), 135.4 (C), 133.5 (C), 129.5 (C), 128.6 (CH), 128.5 (CH), 126.9 (CH), 125.8 (CH), 124.3 (CH), 122.7 (CH), 122.2 (CH), 114.2 (CH), 105.4 (CH), 83.7 (C), 51.5 (CH$_3$), 50.8 (CH), 28.1 (CH$_3$), missing carbon attributed to accidental equivalence); HRMS (EI) Calcd for C$_{24}$H$_{25}$NO$_4$ 391.1778, Found 391.1786; HPLC analysis: 98.5% ee (Chiralcel OD-H, 4% iPr—OH in hexanes, 0.8 mL/min, λ=254 nm, $t_R$=8.7 min, major; 15.9 min, minor).

Tert-butyl 4-((S,E)-3-(methoxycarbonyl)-1-(4-bromophenyl)allyl)-1H-indole-1-carboxylate (4c) was prepared using the general procedure set forth above. The product was purified via flash chromatography (silica gel, 7:1 pentane:diethyl ether) to give product as a white solid (0.125 g, 53% yield), mp 71-74° C.; $R_f$ 0.26 (5:1 pentane: diethyl ether); $[\alpha]_D^{25}$ +11.1° (c 1.08, CHCl$_3$); FTIR (neat): 1725 cm$^{-1}$; $^1$H NMR (500 MHz, CDCl$_3$) δ 8.10 (d, J=8.0 Hz, 1H), 7.55 (d, J=3.5 Hz, 1H), 7.46 (dd, J=15.5, 7.0 Hz, 1H), 7.41 (d, J=8.5 Hz, 2H), 7.28 (m, 1H), 7.04 (d, J=8.5 Hz, 2H), 6.99 (d, J=7.5 Hz, 1H), 6.38 (d, J=4.0 Hz, 1H), 5.70 (dd, J=15.5, 1.5 Hz, 1H), 5.18 (d, J=7.0 Hz, 1H), 3.73 (s, 3H), 1.66 (s, 9H); $^{13}$C NMR (75 MHz, CDCl$_3$) δ 166.7 (C), 149.5 (C), 148.8 (CH), 140.1 (C) 135.5 (C), 132.8 (C), 131.7 (CH), 130.2 (CH), 129.4 (C), 126.1 (CH), 124.4 (CH), 123.1 (CH), 122.2 (CH), 120.9 (C), 114.5 (CH), 105.2 (CH), 83.9 (C), 51.6 (CH$_3$), 50.2 (CH), 28.1 (CH$_3$); HPLC analysis: 98.77% ee (Chiralpak AD-RH, 4% iPr—OH in hexanes, 0.8 mL/min, λ=254 nm, $t_R$=11.2 min, major; 13.3 min, minor).

Tert-butyl 4-((S,E)-3-(methoxycarbonyl)-1-(3,4-dichlorophenyl)allyl)-1H-indole-1-carboxylate (4d) was prepared using the general procedure set forth above. The product was purified via flash chromatography (silica gel, 6:1 pentane:diethyl ether) to give product as a white solid (0.104 g, 45% yield), mp 64-67° C.; $R_f$ 0.22 (5:1 pentane:diethyl ether); $[\alpha]_D^{25}$ +12.9° (c 1.02, CHCl$_3$) FTIR (neat): 1725 cm$^{-1}$; $^1$H NMR (400 MHz, CDCl$_3$) δ 8.12 (d, J=8.4 Hz, 1H), 7.57 (d, J=3.6 Hz, 1H), 7.43 (dd, J=15.6, 6.8 Hz, 1H), 7.36 (d, J=8.4 Hz, 1H), 7.32-7.25 (m, 2H), 7.01-6.98 (m, 2H), 6.38 (d, J=4.0 Hz, 1H), 5.72 (dd, J=15.6, 1.6 Hz, 1H), 5.18 (d, J=6.8 Hz, 1H), 3.74 (s, 3H), 1.66 (s, 9H); $^{13}$C NMR (75 MHz, CDCl$_3$) δ 166.5 (C), 149.5 (C), 148.1 (CH), 141.3 (C), 135.5 (C), 132.7 (C), 132.2 (C), 131.1 (CH), 130.5 (CH), 130.4 (CH), 129.3 (C), 127.9 (CH), 126.2 (CH), 124.5 (CH), 123.4 (CH), 122.1 (CH), 114.7 (CH), 105.0 (CH), 83.9 (C), 51.6 (CH$_3$), 49.8 (CH), 28.1 (CH$_3$); HPLC analysis: 98.0% ee (Chiralpak AD-RH, 2% iPr—OH in hexanes, 0.8 mL/min, λ=254 nm, $t_R$=8.4 min, major; 11.1 min, minor).

Tert-butyl 4-((S,E)-3-(methoxycarbonyl)-1-(naphthalen-2-yl)allyl)-1H-indole-1-carboxylate (4e) was prepared using the general procedure set forth above. The product was purified via flash chromatography (silica gel, 7:1 pentane:diethyl ether) to give product as a light yellow solid (0.123 g, 56% yield), mp 75-78° C.; $R_f$ 0.23 (5:1 pentane:diethyl ether); $[\alpha]_D^{25}$ −18.4° (c 1.11, CHCl3); FTIR (neat): 1725, 1346 cm$^{-1}$; $^1$H NMR (500 MHz, CDCl3) δ 8.11 (d, J=7.5 Hz, 1H), 7.80-7.74 (m, 3H), 7.64 (s, 1H), 7.60 (dd, J=16.0, 7.0 Hz, 1H), 7.52 (d, J=3.0 Hz, 1H), 7.47-7.42 (m, 2H), 7.31-7.24 (m, 2H), 7.05 (d, J=8.0 Hz, 1H), 6.45 (d, J=4.0 Hz, 1H), 5.76 (dd, J=16.0, 1.5 Hz, 1H), 5.40 (d, J=6.5 Hz, 1H), 3.72 (s, 3H), 1.65 (s, 9H); $^{13}$C NMR (75 MHz, CDCl$_3$) δ 166.8 (C), 149.6 (C), 149.4 (CH), 138.5 (C), 135.5 (C), 133.4 (C), 133.3 (C), 132.4 (C), 129.6 (CH), 128.3 (CH), 127.8 (CH), 127.6 (CH), 127.0 (CH), 126.9 (CH), 126.2 (CH), 125.9 (CH), 125.8 (CH), 124.4 (CH), 122.9 (CH), 122.4 (CH), 114.3 (CH), 105.5 (CH), 83.8 (C), 51.5 (CH$_3$), 50.9 (CH), 28.1 (CH$_3$); HPLC analysis: 98.0% ee (Chiralpak AD-RH, 2% iPr—OH in hexanes, 0.8 mL/min, λ=254 nm, $t_R$=14.0 min, major; 17.0 min, minor); Anal. Calcd for C$_{28}$H$_{27}$NO$_4$: C, 76.17; H, 6.16; N, 3.17. Found: C, 75.82; H, 6.26; N, 3.20.

Tert-butyl 4-((S,E)-3-(methoxycarbonyl)-1-(4-methoxyphenyl)allyl)-1H-indole-1-carboxylate (4b) was prepared using the general procedure set forth above. The product was purified via flash chromatography (silica gel, 5:1 pentane: diethyl ether) to give the product as a white solid (0.109 g, 52% yield), mp 70-73° C.; $R_f$ 0.16 5:1 pentane:diethyl ether); $[\alpha]_D^{25}$ +18.9° (c 1.29, CHCl$_3$); FTIR (neat): 1723 cm$^{-1}$; $^1$H NMR (500 MHz, CDCl$_3$) δ 8.08 (d, J=8.0 Hz, 1H), 7.54 (d, J=4.0 Hz, 1H), 7.49 (dd, J=15.5, 7.0 Hz, 1H), 7.27 (appt. t, J=8.0 Hz, 1H), 7.08 (d, J=8.5 Hz, 2H), 7.00 (d, J=7.0 Hz, 1H), 6.83 (d, J=8.5 Hz, 2H), 6.42 (d, J=4.0 Hz, 1H), 5.70 (dd, J=15.5, 1.5 Hz, 1H), 5.18 (d, J=7.0 Hz, 1H), 3.77 (s, 3H), 3.72 (s, 3H), 1.65 (s, 9H); $^{13}$C NMR (125 MHz, CDCl$_3$) δ 166.9 (C), 158.4 (C), 150.0 (CH), 149.6 (C), 135.4 (C), 133.8 (C), 133.0 (C), 129.5 (CH), 129.4 (C), 125.8 (C), 124.3 (CH), 122.4 (CH), 122.1 (CH), 114.1 (CH), 113.9 (CH), 105.5 (CH), 83.7 (C), 55.2 (CH$_3$), 51.5 (CH$_3$), 50.0 (CH), 28.1 (CH$_3$); HPLC analysis: 98.0% ee (Chiralpak AD-RH, 4% iPr—OH in hexanes, 0.8 mL/min, λ=254 nm, $t_R$=9.0 min, major; 11.6 min, minor); Anal. Calcd for C$_{25}$H$_{27}$NO$_5$: C, 71.24; H, 6.46; N, 3.32. Found: C, 71.14; H, 6.57; N, 3.38.

Tert-butyl 4-((R,E)-4-(methoxycarbonyl)but-3-en-2-yl)-1H-indole-1-carboxylate (4h) was prepared using the general procedure set forth above. The product was purified via flash chromatography (silica gel, 7:1 pentane:diethyl ether) to give the product as a clear oil (0.100 g, 61% yield), $R_f$ 0.32 (5:1 pentane:diethyl ether); FTIR (neat): 1724 cm$^{-1}$; $^1$H NMR (500 MHz, CDCl$_3$) δ 8.06 (d, J=8.0 Hz, 1H), 7.61 (d, J=3.5 Hz, 1H), 7.28 (appt. t, J=8.0 Hz, 1H), 7.21 (dd, J=16.0 6.5 Hz, 1H), 7.06 (d, J=8.0 Hz, 1H), 6.60 (d, J=3.5 Hz, 1H), 5.82 (dd, J=16.0 1.5 Hz, 1H), 4.01 (m, 1H), 3.70 (s, 3H), 1.67 (s, 9H) 1.53 (d, J=7.0 Hz, 3H); $^{13}$C NMR (75 MHz, CDCl$_3$) δ 167.2 (C), 152.4 (C), 149.7 (C), 135.4 (C), 129.1 (C), 125.8 (CH), 124.6 (CH), 120.3 (CH), 120.0 (CH), 113.9 (CH), 105.2 (CH), 83.8 (C), 51.5 (CH$_3$), 39.1 (CH), 28.2 (CH$_3$) 19.5 (CH$_3$), missing carbon attributed to accidental equivalence; LCMS (ESI) m/z (relative intensity): 329.9 (68), 274.0 (73); HRMS (ESI) Calcd for [C$_{19}$H$_{23}$NO$_4$Na]$^+$ (M+Na)$^+$: 352.1519, Found 352.1510; HPLC analysis: 98.6% ee (Chiralpak AD-RH, 0.5% iPr—OH in hexanes, 0.8 mL/min, λ=254 nm, $t_R$=11.0 min, major; 14.5 min, minor).

Tert-butyl 4-((R,E)-3-(methoxycarbonyl)-1-(1-tert-butoxycarbonyl-1H-indol-3-yl)allyl)-1H-indole-1-carboxylate (4f) was prepared using the general procedure set forth above. The product was purified via flash chromatography (silica gel, 7:1 pentane:diethyl ether) to give product as a light yellow solid (0.170 g, 64% yield), mp 104-107° C.; $R_f$ 0.18 (5:1 pentane:diethyl ether); $[\alpha]_D^{25}$ −28.5° (c 1.44, CHCl$_3$); FTIR (neat): 1725, 1153 cm$^{-1}$; $^1$H NMR (500 MHz, CDCl$_3$) δ 8.09 (m, 2H), 7.59 (d, J=3.5 Hz, 1H), 7.49 (dd, J=15.5, 7.0 Hz, 1H), 7.33 (s, 1H), 7.29-7.21 (m, 3H), 7.12-7.08 (m, 1H), 7.04 (d, J=7.0 Hz, 1H), 6.59 (d, J=3.5 Hz, 1H), 5.77 (dd, J=15.5, 1.5 Hz, 1H), 5.38 (d, J=7.0 Hz, 1H), 3.71 (s, 3H), 1.67 (s, 9H), 1.66 (s, 9H); $^{13}$C NMR (75 MHz, CDCl$_3$) δ 166.7 (C), 149.7 (C), 149.5 (C), 148.1 (CH), 135.6 (C), 135.4 (C), 131.9 (C), 129.5 (C), 129.4 (C), 126.0 (CH), 124.5 (CH), 124.4 (CH), 124.0 (CH), 122.54 (CH), 122.49 (CH), 122.1 (CH), 120.6 (C), 119.5 (CH), 115.2 (CH), 114.3 (CH), 105.1 (CH), 83.8 (C), 83.7 (C), 51.5 (CH$_3$), 42.2 (CH), 28.11 (CH$_3$), 28.08 (CH$_3$); HPLC analysis: 97.7% ee (Chiralpak AD-RH, 2% iPr—OH in hexanes, 0.8 mL/min, λ=254 nm, $t_R$=8.3 min, major; 12.3 min, minor).

Tert-butyl 4-((R,1E,4E)-1-(methoxycarbonyl)-5-phenylpenta-1,4-dien-3-yl)-1H-indole-1-carboxylate (4g) was prepared using the general procedure set forth above. The product was purified via flash chromatography (silica gel, 7:1 pentane:diethyl ether) to give product as a sticky white solid (0.117 g, 56% yield), $R_f$ 0.27 (5:1 pentane:diethyl ether); $[\alpha]_D^{25}$ −22.2° (c 1.27, CHCl$_3$); FTIR (neat): 1724 cm$^{-1}$; $^1$H NMR (500 MHz, CDCl$_3$) δ 8.10 (d, J=8.0 Hz, 1H), 7.61 (d, J=3.5 Hz, 1H), 7.36-7.28 (m, 6H), 7.24-7.21 (m, 1H), 7.11 (d, J=7.0 Hz, 1H), 6.63 (d, J=4.0 Hz, 1H), 6.47 (d, J=3.0 Hz, 2H), 5.90 (dd, J=15.5, 1.5 Hz, 1H), 4.73 (m, 1H), 3.73 (s, 3H), 1.67 (s, 9H); $^{13}$C NMR (75 MHz, CDCl$_3$) δ 166.8 (C), 149.6 (C), 149.2 (CH), 136.8 (C), 135.5 (C), 132.7 (C), 132.0 (CH), 129.3 (C), 129.2 (CH), 128.5 (CH), 127.6 (CH), 126.3 (CH), 126.0 (CH), 124.5 (CH), 121.9 (CH), 121.7 (CH), 114.3 (CH), 105.3 (CH), 83.8 (C), 51.5 (CH$_3$), 48.2 (CH), 28.2 (CH$_3$); LCMS (ESI) m/z (relative intensity): 417.9 (100), 318.1 (65); HRMS (ESI) Calcd for $[C_{26}H_{21}NO_4Na]^+$ (M+Na)+: 440.1832, Found 440.1820; HPLC analysis: 99.0% ee (Chiralcel OD-H, 2% iPr—OH in hexanes, 0.8 mL/min, λ=254 nm, $t_R$=13.6 min, major; 19.9 min, minor).

Example 7

Synthesis of 6,7-dihydro-2-nitrobenzo-[b]thiophen-4(5H)-one 6,7-Dihydro-2-nitrobenzo[b]thiophen-4(5H)-one:

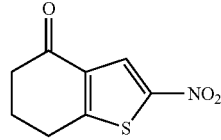

was prepared using a literature procedure (Asprou et al., *J. Heterocyclic Chem.*, 17:87-92 (1980) ("Asprou"), which is hereby incorporated by reference). To a 50 mL round bottom flask charged with a stir bar was added 4-keto-4,5,6,7-tetrahydrothianaphthene (0.61 g, 4 mmole) and concentrated sulfuric acid (6 mL). The solution was then cooled in an ice/salt bath to −5° C. and stirred while a solution of concentrated nitric acid (0.3 mL) in concentrated sulfuric acid (3 mL) was added dropwise over 30 minutes. Solution was stirred for another 50 minutes and allowed to gradually warm to 5° C. The reaction mixture was then poured onto crushed ice and the yellow precipitate filter and washed with several portions of ice-cold water to give product as a yellow solid (0.594 g, 75% yield). Spectral data were consistent with the literature values (Asprou, which is hereby incorporated by reference).

Example 8

Synthesis of 6,7-dihydro-2-nitrobenzo-[b]thiophen-4-yl acetate 6,7-Dihydro-2-nitrobenzo[b]thiophen-4-yl acetate (7) was prepared using a modified literature procedure (Maekawa, which is hereby incorporated by reference). To a flame-dried 100 mL round bottom flask charged with a stir bar was added 6,7-dihydro-2-nitrobenzo[b]thiophen-4-yl acetate (0.40 g, 2.0 mmole), isopropenyl acetate (75 mL), and p-toluenesulfonic acid monohydrate (50 mg, 0.26 mmole). The solution was refluxed for 8 hours during which time the solvent was slowly distilled off at a rate of 7 mL/hour. The solution was then allowed to cool to ambient temperature and a solution of 1:1 diethyl ether:saturated aqueous NaHCO$_3$ was added. The layers were separated and the aqueous layer was extracted with diethyl ether (30 mL). The combined ether layers were then washed with saturated aqueous NaHCO$_3$ (2×25 mL), brine (25 mL), and dried over anhydrous MgSO$_4$. The solution was then filtered through a plug of silica gel, concentrated in vacuo and the residue purified via flash chromatography (silica gel, 3:1 pentane:diethyl ether) to give product as a sticky yellow solid (0.215 g, 45% yield), $R_f$ 0.36 (1:1 pentane:diethyl ether); FTIR (neat): 1759, 1319 cm$^{-1}$; $^1$H NMR (500 MHz, CDCl$_3$) δ 7.59 (s, 1H), 5.64 (t, J=4.7 Hz, 1H), 2.96 (t, J=8.7 Hz, 2H), 2.63 (td, J=8.7 4.7 Hz, 2H), 2.29 (s, 3H); $^{13}$C NMR (75 MHz, CDCl$_3$) δ 168.8 (C), 145.5 (C), 141.6 (C), 131.9 (C), 122.9 (CH), 112.8 (CH), 22.9 CH$_2$), 22.4 (CH$_2$) 20.7 (CH$_3$), missing peak attributed to nitro-bearing carbon.

Example 9

Procedures for C—H/Cope-Elimination to Form Benzothiophenes (S,E)-Methyl 4-(2-nitrobenzo[b]thiophen-4-yl)-4-phenyl-but-2-enoate (8) was prepared using the general procedure set forth above. The product was purified via flash chromatography (silica gel, 4:1-2:1 pentane:diethyl ether) to give product as a yellow solid (0.158 g, 89% yield), mp 50-53° C.; $R_f$ 0.38 (1:1 pentane:diethyl ether); $[α]_D^{25}$ −31.5° (c 0.71, CHCl$_3$); FTIR (neat): 1718, 1341, 1322 cm$^{-1}$; $^1$H NMR (400 MHz, CDCl$_3$) δ 8.06 (s, 1H), 7.66 (d, J=8.0 Hz, 1H), 7.45 (t, J=8.0 Hz, 1H), 7.38 (dd, J=15.6 6.8 Hz, 1H), 7.26-7.23 (m, 2H), 7.20-7.16 (m, 2H), 7.08 (d, J=7.2 Hz, 2H), 5.60 (dd, J=15.6, 1.2 Hz, 1H), 5.27 (d, J=6.8 Hz, 1H), 3.65 (s, 3H); $^{13}$C NMR (75 MHz, CDCl$_3$) δ 166.4 (C), 151.4 (C), 148.3 (CH), 141.3 (C), 139.9 (C), 139.7 (C), 135.1 (C), 129.3 (CH), 129.0 (CH), 128.5 (CH), 127.6 (CH), 125.8 (CH), 123.7 (CH), 123.4 (CH), 121.9 (CH), 51.7 (CH$_3$), 50.8 (CH); LCMS (ESI) m/z (relative intensity): 376.0 (100); HRMS (ESI) Calcd for $C_{19}H_{15}NSO_4Na$ 376.0614, Found 376.0616; HPLC analysis: 99.0% ee (Chiralpak AS-H, 10% iPr—OH in hexanes, 0.7 mL/min, λ=254 nm, $t_R$=30.8 min, major; 26.7 min, minor).

Example 10

Synthesis of 2-carboxyethyltriphenyl-phosphonium chloride

2-Carboxyethyltriphenylphosphonium chloride (11):

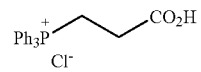

was prepared according to the literature procedure (Maekawa, which is hereby incorporated by reference) and gave $^1$H NMR data identical to the published values (Maekawa, which is hereby incorporated by reference).

Example 11

Synthesis of Arylvinyldiaozacetates

The following protocol for the synthesis of 3a is typical for the preparation of all of the methyl arylvinyldiaozacetates 3b-3e.

A solution of KOt-Bu (1.46 g, 13 mmol) in THF (14 mL) was added at 0° C. via syringe into a mixture of benzaldehyde (0.531 g, 5 mmol) and 2-carboxyethyltriphenylphosphonium chloride (11) (2.22 g, 6.0 mmol) in THF (12 mL) over 15 minutes. Stirring was continued for 15 minutes at 0° C. and for 2 hours at ambient temperature under argon.

Dimethyl sulfate (1.26 g, 10 mmol) was added at ambient temperature and stirring was continued for 15 hours under argon. DBU (1.52 g, 10 mmol) was slowly added with cooling in an ice bath. p-ABSA (1.80g, 7.5 mmol) was then added in several portions at 0° C. over 5 minutes. Stirring continued for 2 hours at 0° C. under argon. The solvent was removed in vacuo, and the residue was diluted with cold water (10 mL), dichloromethane (20 mL), and saturated NH₄Cl solution (20 mL). The organic layer was washed once with saturated NH₄Cl, dried over magnesium sulfate, filtered, and then concentrated to about 10 mL. Flash chromatography (silica gel, pentane: diethyl ether, 9:1) gave diazo compound (E)-methyl 2-diazo-4-phenylbut-3-enoate (3a) (0.45 g, 45% yield over three steps) as a red oil. $^1$H NMR data was identical to the literature values.

(E)-Methyl 2-diazo-4-(4-bromophenyl)but-3-enoate (3c) was prepared using the general procedure set forth above. The product was purified via flash chromatography (silica gel, pentane:diethyl ether, 10:1) to give 3c as a red solid (0.829 g, 59% yield), $R_f$ 0.36 (9:1 petroleum ether/diethyl ether); FTIR (neat): 3010, 2953, 2845, 2078, 1705, 1626 cm$^{-1}$; $^1$H NMR (500 MHz, CDCl₃) δ 7.43 (d, J=8.5 Hz, 2H), 7.21 (d, J=8.5 Hz, 2H), 6.48 (d, J=16.5 Hz, 1H), 6.13 (d, J=16.5 Hz, 1H), 3.85 (s, 3H); $^{13}$C NMR (75 MHz, CDCl3) δ 165.2 (C), 135.6 (C), 131.7 (CH), 127.2 (CH), 121.6 (CH), 120.6 (C), 112.1 (CH), 52.2 (CH₃), missing carbon attributed to C═N2; HRMS (EI) Calcd for C₁₁H₉N₂O₂Br 279.9847. Found 279.9824.

(E)-Methyl 2-diazo-4-(4-methoxyphenyl)but-3-enoate (3b) was prepared using the general procedure set forth above. The product was purified via flash chromatography (silica gel, pentane:diethyl ether, 7:1) to give 3b as a red solid (0.754 g, 65% yield), $R_f$ 0.23 (9:1 pentane/diethyl ether); FTIR (neat): 3041, 3009, 2956, 2834, 2072, 1694 cm$^{-1}$; $^1$H NMR (500 MHz, CDCl₃) δ 7.29 (d, J=8.8 Hz, 2H), 6.86 (d, J=8.8 Hz, 2H), 6.29 (d, J=16.0 Hz, 1H), 6.14 (d, J=16.0 Hz, 1H), 3.84 (s, 3H), 3.80 (s, 3H); $^{13}$C NMR (75 MHz, CDCl₃) δ 165.8 (C), 158.8 (C), 129.6 (C), 127.0 (CH), 122.7 (CH), 114.1 (CH), 108.5 (CH), 55.2 (CH₃), 52.2 (CH₃), missing carbon attributed to C═N2; HRMS (EI) Calcd for C₁₂H₁₂N₂O₃ 232.0848. Found 232.0867.

(E)-Methyl 2-diazo-4-(3,4-dichlorophenyl)but-3-enoate (3d) was prepared using the general procedure set forth above. The product was purified via flash chromatography (silica gel, pentane:diethyl ether, 10:1) to give 8d as a red solid (0.623 g, 46% yield), $R_f$ 0.30 (9:1 petroleum ether/diethyl ether); FTIR (neat): 3051, 3000, 2954, 2149, 2086, 1697 cm$^{-1}$; $^1$H NMR (500 MHz, CDCl₃) δ 7.41 (d, J=2.0 Hz, 1H), 7.35 (d, J=8.5 Hz, 1H), 7.16 (dd, J=8.5, 2.0 Hz, 1H), 6.48 (d, J=16.5 Hz, 1H), 6.10 (d, J=16.5 Hz, 1H), 3.86 (s, 3H); $^{13}$C NMR (125 MHz, CDCl₃) δ 164.9 (C), 136.8 (C), 132.6 (C), 130.35 (CH), 130.28 (C), 127.2 (CH), 124.7 (CH), 120.1 (CH), 113.6 (CH), 52.3 (CH₃), missing carbon attributed to C═N2; HRMS (EI) Calcd for C₁₁H₈N₂O₂C₁₂ 269.9963. Found 269.9972.

(E)-Methyl 2-diazo-4-(naphthalen-3-yl)but-3-enoate (3e) was prepared using the general procedure set forth above. The product was purified via flash chromatography (silica gel, pentane:diethyl ether, 9:1->7:1) to give 3e as a red solid (0.697 g, 55% yield), $R_f$ 0.31 (9:1 pentane/diethyl ether); FTIR (neat): 3057, 3020, 2946, 2120, 2093, 1705 cm$^{-1}$; $^1$H NMR (500 MHz, CDCl₃) δ 7.80-7.78 (m, 3H), 7.69 (s, 1H), 7.60 (dd, J=9.0, 1.8 Hz, 1H), 7.47-7.41 (m, 2H), 6.60 (d, J=16.5 Hz, 1H), 6.36 (d, J=16.5 Hz, 1H), 3.88 (s, 3H); $^{13}$C NMR (75 MHz, CDCl₃) δ 165.4 (C), 134.2 (C), 133.5 (C), 132.5 (C), 128.2 (CH), 127.8 (CH), 127.5 (CH), 126.2 (CH), 125.6 (CH), 125.3 (CH), 122.99 (CH), 122.95 (CH), 111.3 (CH), 52.1 (CH₃), missing carbon attributed to C═N2; HRMS (EI) Calcd for C₁₅H₁₂N₂O₂ 252.0899. Found 252.0899.

Tert-butyl 3-((E)-3-(methoxycarbonyl)-3-diazoprop-1-enyl)-1H-indole-1-carboxylate (3f) was prepared using the general procedure set forth above. The product was purified via flash chromatography (silica gel, pentane:diethyl ether, 7:1) to give 3f as a red solid (0.840 g, 49% yield), $R_f$ 0.26 (9:1 pentane/diethyl ether); FTIR (neat) 2079, 1734 cm$^{-1}$; $^1$H NMR (500 MHz, CDCl₃) δ 8.17 (m, 1H), 7.77 (d, J=8.0 Hz, 1H), 7.60 (s, 1H), 7.35 (t, J=7.5 Hz, 1H), 7.29 (t, J=7.5 Hz, 1H), 6.52 (d, J=16.5 Hz, 1H), 6.32 (d, J=16.5 Hz, 1H), 3.87 (s, 3H), 1.67 (s, 9H); $^{13}$C NMR (75 MHz, CDCl₃) δ 165.4 (C), 149.2 (C), 135.7 (C), 128.1 (C), 124.6 (CH), 122.8 (CH), 122.6 (CH), 119.4 (CH), 118.3 (C), 115.2 (CH), 114.4 (CH), 110.5 (CH), 83.6 (C), 52.0 (CH₃), 27.9 (CH₃), missing carbon attributed to C═N2; HRMS (EI) Calcd for C18H19N₃O₄ 341.1370. Found 341.1369; Anal. Calcd for C₁₈H₁₉N₃O₄: C, 63.33; H, 5.61. Found: C, 63.57; H, 5.77.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A method for making a 4-substituted indole, benzofuran, benzothiophene, benzimidazole, benzoxazole, or benzothiazole, said method comprising:

providing a 4-substituted-6,7-dihydro indole, benzofuran, benzothiophene, benzimidazole, benzoxazole, or benzothiazole compound having the formula:

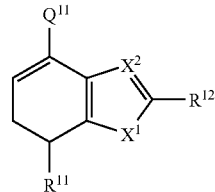

wherein $Q^{11}$ is a leaving group; wherein $X^1$ is N-$Q^{12}$, O, or S; wherein $Q^{12}$ is an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group an aryl group, a carboxylic ester group, an amide group, a aldehyde group, an alkylcarbonyl group, an arylcarbonyl group an alkyloxycarbonyl group, or an aryloxycarbonyl group, an unsubstituted, monosubstitued, or disubstituted amine, an alkoxy group, an alkylthio group, an arylthio group, and a nitro group; and wherein $R^{12}$ and $R^3$ are independently selected from a hydrogen atom, a halogen atom, an alkyl group, an aryl group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, an alkylthio group, an arylthio group, and a nitro group, or wherein $R^{12}$ and $R^3$, taken together with the carbon atoms to which they are bonded, form a 5-12 membered ring;

providing a diazovinyl compound having the formula:

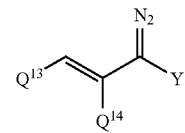

wherein $Q^{13}$ is an alkyl group or an aryl group, and wherein $Q^{14}$ is a hydrogen atom, an alkyl group, or an aryl group; or wherein $Q^{13}$ and $Q^{14}$, taken together with the carbon atoms to which they are bonded, form a 5-12 membered ring (e.g., a substituted or unsubstituted cyclopentene or cyclohexene ring); and wherein Y is an electron withdrawing group; and contacting the 4-substituted-6,7-dihydro indole, benzofuran, benzothiophene, benzimidazole, benzoxazole, or benzothiazole compound with the vinyldiazo compound in the presence of a dirhodium catalyst under conditions effective to produce a compound having the formula:

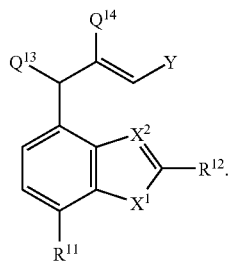

2. A method according to claim 1, wherein $Q^{11}$ is selected from a halogen atom, an alkyl sulfonate group, an aryl sulfonate group, and an acyloxy group.

3. A method according to claim 1, wherein the 4-substituted indole, benzofuran, benzothiophene, benzimidazole, benzoxazole, or benzothiazole is a 4-substituted indole; wherein the 4-substituted-6,7-dihydro indole, benzofuran, benzothiophene, benzimidazole, benzoxazole, or benzothiazole compound is a 4-substituted-6,7-dihydro indole having the formula:

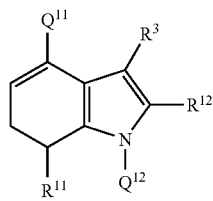

and wherein said contacting is carried out in the presence of a dirhodium catalyst under conditions effective to produce a compound having the formula:

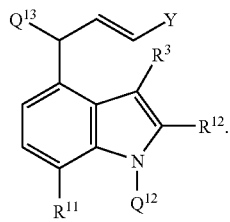

4. A method according to claim 1, wherein the 4-substituted indole, benzofuran, benzothiophene, benzimidazole, benzoxazole, or benzothiazole is a 4-substituted benzofuran; wherein the 4-substituted-6,7-dihydro indole, benzofuran, benzothiophene, benzimidazole, benzoxazole, or benzothiazole compound is a 4-substituted-6,7-dihydro benzofuran having the formula:

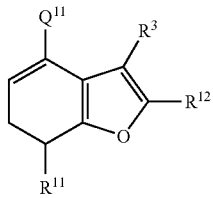

and wherein said contacting is carried out in the presence of a dirhodium catalyst under conditions effective to produce a compound having the formula:

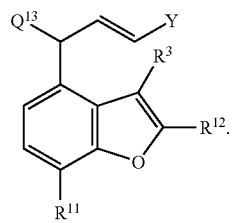

5. A method according to claim 1, wherein the 4-substituted indole, benzofuran, benzothiophene, benzimidazole, benzoxazole, or benzothiazole is a 4-substituted benzothiophene; wherein the 4-substituted-6,7-dihydro indole, benzofuran, benzothiophene, benzimidazole, benzoxazole, or benzothiazole compound is a 4-substituted-6,7-dihydro benzothiophene having the formula:

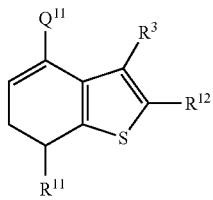

and wherein said contacting is carried out in the presence of a dirhodium catalyst under conditions effective to produce a compound having the formula:

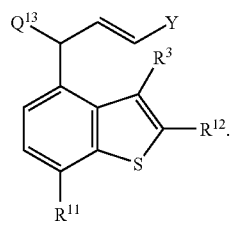

6. A method according to claim 1, wherein the 4-substituted indole, benzofuran, benzothiophene, benzimidazole, benzoxazole, or benzothiazole is a 4-substituted benzimidazole; wherein the 4-substituted-6,7-dihydro indole, benzofuran, benzothiophene, benzimidazole, benzoxazole, or benzothiazole compound is a 4-substituted-6,7-dihydro benzimidazole having the formula:

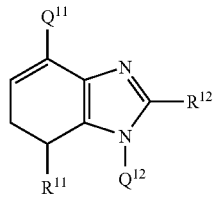

and wherein said contacting is carried out in the presence of a dirhodium catalyst under conditions effective to produce a compound having the formula:

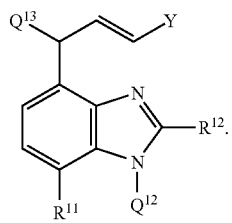

7. A method according to claim 1, wherein the 4-substituted indole, benzofuran, benzothiophene, benzimidazole, benzoxazole, or benzothiazole is a 4-substituted benzoxazole; wherein the 4-substituted-6,7-dihydro indole, benzofuran, benzothiophene, benzimidazole, benzoxazole, or benzothiazole compound is a 4-substituted-6,7-dihydro benzoxazole having the formula:

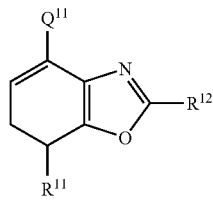

and wherein said contacting is carried out in the presence of a dirhodium catalyst under conditions effective to produce a compound having the formula:

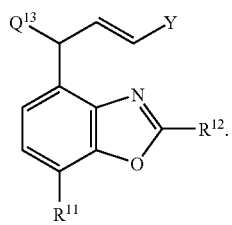

8. A method according to claim 1, wherein the 4-substituted indole, benzofuran, benzothiophene, benzimidazole, benzoxazole, or benzothiazole is a 4-substituted benzothiazole; wherein the 4-substituted-6,7-dihydro indole, benzofuran, benzothiophene, benzimidazole, benzoxazole, or benzothiazole compound is a 4-substituted-6,7-dihydro benzothiazole having the formula:

and wherein said contacting is carried out in the presence of a dirhodium catalyst under conditions effective to produce a compound having the formula:

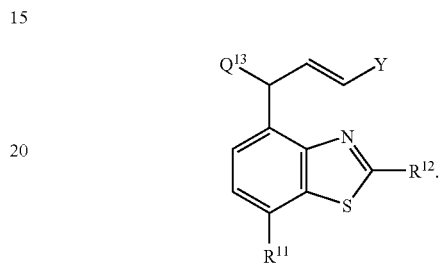

9. A method according to claim 1, wherein, the dirhodium catalyst has $D_2$ symmetry.

10. A method according to claim 1, wherein the dirhodium catalyst is a dirhodium tetracarboxylate catalyst.

11. A method according to claim 10, wherein the dirhodium tetracarboxylate catalyst has the formula:

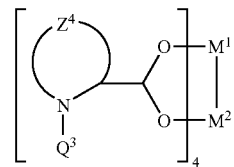

wherein each of $M^1$ and $M^2$ is Rh; $Z^4$ represents the atoms necessary to complete a 3-12 membered heterocyclic ring; and $Q^3$ is an electron withdrawing group.

12. A method according to claim 11, wherein $Z^4$ is a —$CH_2CH_2CH_2$— group and wherein $Q^3$ is a 4-dodecylphenylsulfonyl moiety.

13. A method according to claim 1, wherein the dirhodium catalyst is a dirhodium tetracarboxamidate catalyst.

14. A method according to claim 13, wherein the dirhodium tetracarboxamidate catalyst has the formula:

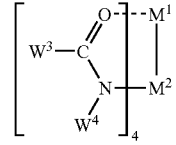

wherein each of $M^1$ and $M^2$ is Rh; wherein $W^3$ represents an alkyl group, an aryl group, an alkoxy group, or an amine group and wherein $W^4$ represents an alkyl group or an aryl group; or wherein $W^3$ and $W^4$, taken together with the atoms to which they are bonded, form a 3-12 membered ring.

15. A method according to claim 1, wherein the dirhodium catalyst has $D_2$ symmetry and wherein said contacting is carried out under conditions effective to selectively produce a compound having the formula:

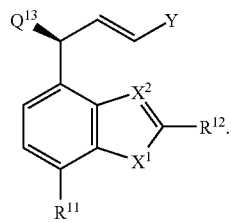

16. A method according to claim 1, wherein the dirhodium catalyst has $D_2$ symmetry and wherein said contacting is carried out under conditions effective to selectively produce a compound having the formula:

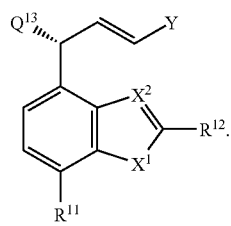

17. A method according to claim 1, wherein $Q^{13}$ is a substituted or unsubstituted, 5-20 membered, heterocyclic or homocyclic ring.

18. A method according to claim 1, wherein $Q^{13}$ has the formula -$Q^5$-$Q^6$, wherein $Q^5$ is a C1-C12 saturated or unsaturated alkylene moiety, optionally containing one or more heteroatoms and wherein $Q^6$ is a substituted or unsubstituted, 5-20 membered, heterocyclic or homocyclic ring.

19. A method according to claim 18, wherein -$Q^5$- is an unsaturated alkylene moiety having the formula —CH=CH—.

20. A method according to claim 1, wherein Y is a carboxylic ester group.

21. A compound having the formula:

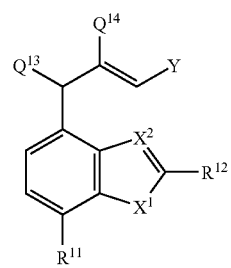

wherein $X^1$ is N-$Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring; and wherein Y is an electron withdrawing group.

22. A compound according to claim 21, wherein said compound has the formula:

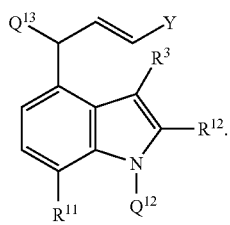

23. A compound according to claim 21, wherein said compound has the formula:

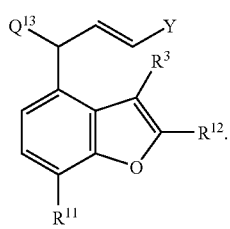

24. A compound according to claim 21, wherein said compound has the formula:

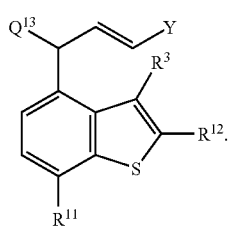

25. A compound according to claim 21, wherein said compound has the formula:

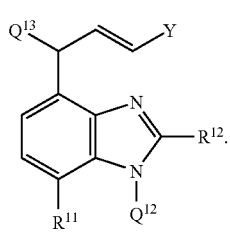

26. A compound according to claim 21, wherein said compound has the formula:

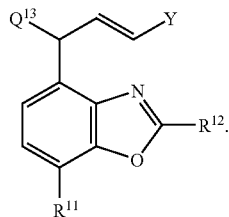

27. A compound according to claim 21, wherein said compound has the formula:

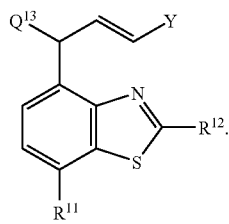

28. A compound according to claim 21 that is enriched in an enantiomer having the formula:

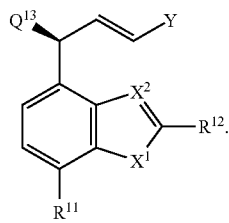

29. A compound according to claim 21 that is enriched in an enantiomer having the formula:

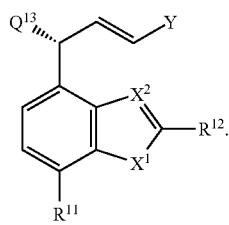

30. A compound according to claim 21, wherein $Q^{13}$ is a substituted or unsubstituted, 5-20 membered, heterocyclic or homocyclic ring.

31. A compound according to claim 21, wherein $Q^{13}$ has the formula $-Q^5-Q^6$, wherein $Q^5$ is a C1-C12 saturated or unsaturated alkylene moiety, optionally containing one or more heteroatoms and wherein $Q^6$ is a substituted or unsubstituted, 5-20 membered, heterocyclic or homocyclic ring.

32. A compound according to claim 31, wherein $-Q^5-$ is an unsaturated alkylene moiety having the formula —CH=CH—.

33. A compound according to claim 21, wherein Y is a carboxylic ester group.

34. A compound according to claim 21, wherein $R^{11}$ is not a carboxylic acid group, a hydroxy group, or a thiol group; wherein $R^{12}$ is not a carboxylic acid group, a hydroxy group, or a thiol group; and wherein $R^3$ is not a carboxylic acid group, a hydroxy group, or a thiol group.

35. A compound having the formula:

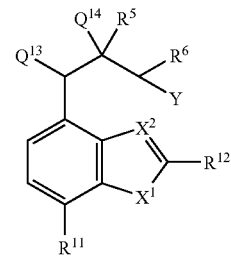

that is enriched in an enantiomer having one of the following formulae:

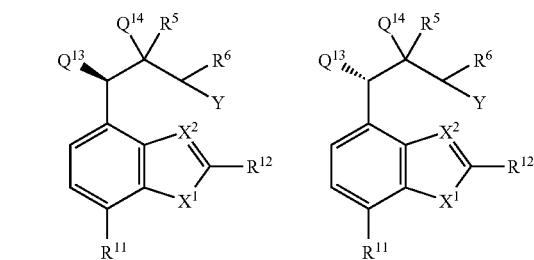

wherein $X^1$ is $N-Q^{12}$, O, or S; wherein $Q^{12}$ is a hydrogen atom, an alkyl group, an aryl group, an alkylcarbonyl group, an arylcarbonyl group, an alkyloxycarbonyl group, an aryloxycarbonyl group, an alkylsulfonyl group, or an arylsulfonyl group; wherein $X^2$ is C—$R^3$ or N; wherein $R^{11}$ is selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group; wherein $R^{12}$ and $R^3$ are independently selected from a hydrogen atom, a halogen atom, an alkyl group, an aryl group, a carboxylic acid group, a carboxylic ester group, an amide group, a aldehyde group, an alkylcarbonyl group, an arylcarbonyl group, an alkyloxycarbonyl group, or an aryloxycarbonyl group, an unsubstituted, monosubstitued, or disubstituted amine, an alkoxy group, a hydroxy group, an alkylthio group, an arylthio group, a thiol group, and a nitro group, or wherein $R^{12}$ and $R^3$, taken together with the carbon atoms to which they are bonded, form a 5-12 membered ring; wherein $Q^{13}$ is an alkyl group or an aryl group; wherein $Q^{14}$ is a hydrogen atom, an alkyl group, or an aryl group; or wherein $Q^{13}$ and $Q^{14}$, taken together with the carbon atoms to which they are bonded, form a 5-12 membered ring; wherein Y is an electron withdrawing group, a aldehyde group, or a —CH$_2$OH or other alkyl group; and wherein each of $R^5$ and $R^6$ is a hydrogen atom, or wherein. $R^5$ and $R^6$, taken together, represent a second bond between the carbon atoms to which they are bonded.

36. A compound according to claim 35, wherein $R^{11}$ is not a carboxylic acid group, a hydroxy group, or a thiol group; wherein $R^{12}$ is not a carboxylic acid group, a hydroxy group, or a thiol group; and wherein $R^3$ is not a carboxylic acid group, a hydroxy group, or a thiol group.

* * * * *